(12) United States Patent
Mark et al.

(10) Patent No.: US 11,864,793 B2
(45) Date of Patent: Jan. 9, 2024

(54) SURGICAL ACCESS ASSEMBLY AND METHOD OF USING SAME

(71) Applicant: Nico Corporation, Indianapolis, IN (US)

(72) Inventors: Joseph L. Mark, Indianapolis, IN (US); Amin Kassam, Ottawa (CA)

(73) Assignee: NICO CORPORATION, Indianapolis, IN (US)

( * ) Notice: Subject to any disclaimer, the term of this patent is extended or adjusted under 35 U.S.C. 154(b) by 138 days.

(21) Appl. No.: 17/115,472

(22) Filed: Dec. 8, 2020

(65) Prior Publication Data
US 2021/0085363 A1 Mar. 25, 2021

Related U.S. Application Data

(63) Continuation of application No. 16/102,416, filed on Aug. 13, 2018, now Pat. No. 11,464,539, which is a
(Continued)

(51) Int. Cl.
*A61B 17/34* (2006.01)
*A61B 90/50* (2016.01)
(Continued)

(52) U.S. Cl.
CPC ...... *A61B 17/3417* (2013.01); *A61B 1/00135* (2013.01); *A61B 1/00165* (2013.01);
(Continued)

(58) Field of Classification Search
CPC ............ A61B 17/3417; A61B 17/0218; A61B 17/320016; A61B 17/32002;
(Continued)

(56) References Cited

U.S. PATENT DOCUMENTS 2,006,358 A 7/1935 Kurkjian
3,690,323 A 9/1972 Wortman et al.
(Continued)

FOREIGN PATENT DOCUMENTS

AU 2018203807 A1 6/2018
DE 10224005 A1 12/2003
(Continued)

OTHER PUBLICATIONS

Canadian Office Action dated Feb. 26, 2021 in Canadian Application No. 3,010,024, 4 pages.
(Continued)

*Primary Examiner* — Peter Luong
(74) *Attorney, Agent, or Firm* — Brooks Kushman, P.C.

(57) ABSTRACT

A surgical access assembly and method of use is disclosed. The surgical access assembly comprises an outer sheath and an obturator. The outer sheath and obturator are configured to be delivered to an area of interest within the brain. Either the outer sheath or the obturator may be configured to operate with a navigational system to track the location of either within the brain. Once positioned at a desired location, the obturator is removed, leaving a distal end of the outer sheath adjacent an area of interest, and creating a working corridor. Interrogation of the area of interest may be performed to evaluate a disorder and/or abnormality, as well as evaluate treatment regimes. Interventional devices may also be introduced to the area of interest, as well as a variety of treatments.

16 Claims, 27 Drawing Sheets

Related U.S. Application Data continuation of application No. 13/474,433, filed on May 17, 2012, now abandoned, which is a continuation-in-part of application No. 13/444,722, filed on Apr. 11, 2012, now Pat. No. 9,579,121, which is a continuation-in-part of application No. 13/280,015, filed on Oct. 24, 2011, now Pat. No. 9,770,261, which is a continuation-in-part of application No. 11/665,666, filed as application No. PCT/US2005/039185 on Oct. 28, 2005, now abandoned.

(60) Provisional application No. 60/623,094, filed on Oct. 28, 2004.

(51) Int. Cl.

| | | |
|---|---|---|
| *A61B 90/98* | (2016.01) | |
| *A61B 1/00* | (2006.01) | |
| *A61B 1/06* | (2006.01) | |
| *A61B 1/313* | (2006.01) | |
| *A61B 1/32* | (2006.01) | |
| *A61B 5/00* | (2006.01) | |
| *A61B 17/32* | (2006.01) | |
| *A61M 39/02* | (2006.01) | |
| *A61B 34/10* | (2016.01) | |
| *A61B 34/20* | (2016.01) | |
| *A61B 90/30* | (2016.01) | |
| *A61B 5/06* | (2006.01) | |
| *A61B 17/02* | (2006.01) | |
| *A61B 90/00* | (2016.01) | |
| *A61M 39/06* | (2006.01) | |
| *A61B 1/04* | (2006.01) | |
| *A61B 90/10* | (2016.01) | |
| *A61B 5/055* | (2006.01) | |
| *A61B 6/12* | (2006.01) | |
| *A61B 6/00* | (2006.01) | |
| *A61B 8/08* | (2006.01) | |
| *A61B 8/12* | (2006.01) | |
| *A61B 17/00* | (2006.01) | |
| *A61B 8/06* | (2006.01) | |
| *A61B 17/3205* | (2006.01) | |

(52) U.S. Cl.
CPC .............. *A61B 1/04* (2013.01); *A61B 1/0607* (2013.01); *A61B 1/0615* (2013.01); *A61B 1/313* (2013.01); *A61B 1/32* (2013.01); *A61B 5/065* (2013.01); *A61B 5/4064* (2013.01); *A61B 17/0218* (2013.01); *A61B 17/32002* (2013.01); *A61B 17/320016* (2013.01); *A61B 17/3421* (2013.01); *A61B 17/3423* (2013.01); *A61B 17/3468* (2013.01); *A61B 34/10* (2016.02); *A61B 34/20* (2016.02); *A61B 90/30* (2016.02); *A61B 90/37* (2016.02); *A61B 90/50* (2016.02); *A61B 90/98* (2016.02); *A61M 39/0247* (2013.01); *A61M 39/06* (2013.01); *A61B 1/00154* (2013.01); *A61B 5/0066* (2013.01); *A61B 5/0071* (2013.01); *A61B 5/0084* (2013.01); *A61B 5/055* (2013.01); *A61B 5/061* (2013.01); *A61B 5/062* (2013.01); *A61B 5/6847* (2013.01); *A61B 6/12* (2013.01); *A61B 6/4417* (2013.01); *A61B 6/501* (2013.01); *A61B 6/5235* (2013.01); *A61B 8/06* (2013.01); *A61B 8/0808* (2013.01); *A61B 8/0841* (2013.01); *A61B 8/12* (2013.01); *A61B 17/0293* (2013.01); *A61B 17/3205* (2013.01); *A61B 90/10* (2016.02); *A61B 90/361* (2016.02); *A61B 2017/00477* (2013.01); *A61B 2017/00907* (2013.01); *A61B 2017/320008* (2013.01); *A61B 2017/320064* (2013.01); *A61B 2017/3405* (2013.01); *A61B 2017/347* (2013.01); *A61B 2017/3454* (2013.01); *A61B 2017/3456* (2013.01); *A61B 2034/2051* (2016.02); *A61B 2034/2055* (2016.02); *A61B 2034/2072* (2016.02); *A61B 2090/062* (2016.02); *A61B 2090/0807* (2016.02); *A61B 2090/0811* (2016.02); *A61B 2090/103* (2016.02); *A61B 2090/309* (2016.02); *A61B 2090/3614* (2016.02); *A61B 2090/3782* (2016.02); *A61B 2090/3937* (2016.02); *A61B 2090/3954* (2016.02); *A61B 2090/3983* (2016.02); *A61M 2039/0205* (2013.01); *A61M 2039/025* (2013.01); *A61M 2039/0264* (2013.01); *A61M 2039/0276* (2013.01); *A61M 2039/0282* (2013.01); *A61M 2039/0626* (2013.01); *A61M 2210/0693* (2013.01)

(58) Field of Classification Search
CPC ............ A61B 17/3421; A61B 17/3423; A61B 17/3468; A61B 17/0293; A61B 17/3205; A61B 1/00135; A61B 1/00165; A61B 1/0607; A61B 1/0615; A61B 1/313; A61B 1/32; A61B 1/00154; A61B 1/04; A61B 1/0684; A61B 5/065; A61B 5/4064; A61B 5/0066; A61B 5/0071; A61B 5/0084; A61B 5/055; A61B 5/061; A61B 5/062; A61B 5/6847; A61B 5/55; A61B 34/10; A61B 34/20; A61B 90/30; A61B 90/37; A61B 90/50; A61B 90/98; A61B 90/10; A61B 90/361; A61B 6/12; A61B 6/4417; A61B 6/501; A61B 6/5235; A61B 6/032; A61B 6/037; A61B 8/06; A61B 8/0808; A61B 8/0841; A61B 8/12; A61B 2017/00477; A61B 2017/00907; A61B 2017/320008; A61B 2017/320064; A61B 2017/3405; A61B 2017/3454; A61B 2017/3456; A61B 2017/347; A61B 2034/2051; A61B 2034/2055; A61B 2034/2072; A61B 2034/107; A61B 2090/062; A61B 2090/0807; A61B 2090/0811; A61B 2090/103; A61B 2090/309; A61B 2090/3614; A61B 2090/3782; A61B 2090/3937; A61B 2090/3954; A61B 2090/3983; A61B 2090/3975; A61M 39/06; A61M 2039/0205; A61M 2039/025; A61M 2039/0264; A61M 2039/0276; A61M 2039/0282; A61M 2039/0626; A61M 2210/0693

See application file for complete search history.

(56) References Cited

U.S. PATENT DOCUMENTS

| | | |
|---|---|---|
| 3,825,007 A | 7/1974 | Rand |
| 4,015,604 A | 4/1977 | Csillag |
| 4,166,389 A | 9/1979 | Montren |
| 4,273,635 A | 6/1981 | Beraud et al. |
| 4,346,703 A | 8/1982 | Dennehey et al. |
| 4,386,602 A | 6/1983 | Sheldon et al. |
| 4,477,256 A | 10/1984 | Hirsch |
| 4,573,981 A | 3/1986 | McFarlane |
| 4,638,798 A | 1/1987 | Shelden et al. |
| 4,655,752 A | 4/1987 | Honkanen et al. |
| 4,675,110 A | 6/1987 | Fay |
| 4,729,070 A | 3/1988 | Chiu |

(56) References Cited

U.S. PATENT DOCUMENTS

| | | | |
|---|---|---|---|
| 4,798,591 A | 1/1989 | Okada | |
| 5,183,464 A | 2/1993 | Dubrul et al. | |
| 5,217,441 A | 6/1993 | Shichman | |
| 5,222,487 A | 6/1993 | Carr et al. | |
| 5,249,568 A | 10/1993 | Brefka et al. | |
| 5,295,952 A | 3/1994 | Pietrafitta | |
| 5,320,611 A | 6/1994 | Bonutti et al. | |
| 5,352,206 A | 10/1994 | Cushieri et al. | |
| 5,397,311 A | 3/1995 | Walker et al. | |
| 5,417,705 A | 5/1995 | Taber et al. | |
| 5,431,638 A | 7/1995 | Hennig et al. | |
| 5,431,676 A | 7/1995 | Dubrul et al. | |
| 5,441,042 A | 8/1995 | Putman | |
| 5,487,739 A | 1/1996 | Aebischer et al. | |
| 5,490,843 A | 2/1996 | Hildwein et al. | |
| 5,599,305 A | 2/1997 | Hermann et al. | |
| 5,669,383 A | 9/1997 | Johnson | |
| 5,676,689 A | 10/1997 | Kensey et al. | |
| 5,716,369 A | 2/1998 | Riza | |
| 5,728,132 A | 3/1998 | Van Tassel et al. | |
| 5,735,865 A | 4/1998 | Schaumann et al. | |
| 5,772,678 A | 6/1998 | Thomason et al. | |
| 5,820,600 A | 10/1998 | Carlson et al. | |
| 5,860,996 A | 1/1999 | Urban et al. | |
| 5,951,494 A | 9/1999 | Wang et al. | |
| 5,967,970 A | 10/1999 | Cowan et al. | |
| 5,989,228 A | 11/1999 | Danks et al. | |
| 6,010,531 A | 1/2000 | Donlon et al. | |
| 6,047,218 A | 4/2000 | Whayne et al. | |
| 6,052,184 A | 4/2000 | Reed | |
| 6,123,667 A | 9/2000 | Poff et al. | |
| 6,129,685 A | 10/2000 | Howard, III | |
| D434,148 S | 11/2000 | Sauer et al. | |
| 6,179,826 B1 | 1/2001 | Aebischer et al. | |
| 6,224,608 B1 | 5/2001 | Ciccolella et al. | |
| 6,226,548 B1 | 5/2001 | Foley et al. | |
| 6,236,875 B1* | 5/2001 | Bucholz | A61B 17/1739 600/407 |
| 6,245,052 B1 | 6/2001 | Orth et al. | |
| 6,280,399 B1 | 8/2001 | Rossin et al. | |
| 6,283,948 B1 | 9/2001 | McKeman et al. | |
| 6,293,952 B1 | 9/2001 | Brosens et al. | |
| 6,309,382 B1 | 10/2001 | Garrison et al. | |
| 6,331,180 B1 | 12/2001 | Cosman et al. | |
| 6,374,135 B1 | 4/2002 | Bucholz | |
| 6,416,520 B1 | 7/2002 | Kynast et al. | |
| 6,537,241 B1 | 3/2003 | Odland | |
| 6,550,952 B1 | 4/2003 | Hulse et al. | |
| 6,551,240 B2 | 4/2003 | Henzler | |
| 6,606,521 B2 | 8/2003 | Paspa et al. | |
| 6,645,178 B1 | 11/2003 | Junker et al. | |
| 6,663,260 B1 | 12/2003 | Tieszen | |
| 6,669,685 B1 | 12/2003 | Rizoiu et al. | |
| 6,676,639 B1 | 1/2004 | Ternstrom | |
| 6,685,630 B2 | 2/2004 | Sauer et al. | |
| 6,761,725 B1 | 7/2004 | Grayzel et al. | |
| 6,782,288 B2 | 8/2004 | Truwit et al. | |
| 6,814,700 B1 | 11/2004 | Mueller et al. | |
| 6,884,253 B1 | 4/2005 | McFarlane | |
| 6,942,634 B2 | 9/2005 | Odland | |
| 6,942,635 B2 | 9/2005 | Rosenblatt et al. | |
| 6,989,003 B2 | 1/2006 | Wing et al. | |
| 7,155,279 B2 | 12/2006 | Whitehurst et al. | |
| 7,160,716 B2 | 1/2007 | Kalina et al. | |
| 7,377,897 B1 | 5/2008 | Kunkel et al. | |
| 7,407,483 B2 | 8/2008 | Perez-Cruet et al. | |
| 7,429,117 B2 | 9/2008 | Pohlert et al. | |
| D611,178 S | 3/2010 | Waring | |
| 7,694,866 B2 | 4/2010 | Shifrin et al. | |
| 7,744,596 B2 | 6/2010 | Young et al. | |
| 7,823,801 B2 | 11/2010 | McGarry et al. | |
| 7,857,271 B2 | 12/2010 | Lees | |
| D630,350 S | 1/2011 | Lin | |
| 7,862,542 B1 | 1/2011 | Harmon, Sr. | |
| 7,945,307 B2 | 5/2011 | Lubock et al. | |
| 8,029,439 B2 | 10/2011 | Todd et al. | |
| 8,192,445 B2 | 6/2012 | Parmer et al. | |
| 8,207,821 B2 | 6/2012 | Roberge et al. | |
| 8,323,185 B2 | 12/2012 | Perez-Cruet et al. | |
| 8,578,884 B2 | 11/2013 | Hawk | |
| 8,960,973 B1 | 2/2015 | Kathawate et al. | |
| 8,992,558 B2 | 3/2015 | Stone et al. | |
| 9,265,523 B2 | 2/2016 | Mark et al. | |
| 9,386,974 B2* | 7/2016 | Wilson | A61B 90/361 |
| 2001/0039430 A1 | 11/2001 | Dubrul et al. | |
| 2001/0050264 A1 | 12/2001 | Schorner | |
| 2002/0103500 A1* | 8/2002 | Gildenberg | A61B 34/30 606/187 |
| 2002/0183594 A1 | 12/2002 | Beane et al. | |
| 2003/0004428 A1 | 1/2003 | Pless et al. | |
| 2003/0045811 A1 | 3/2003 | Hinchliffe et al. | |
| 2003/0045834 A1 | 3/2003 | Wing et al. | |
| 2003/0073934 A1 | 4/2003 | Putz | |
| 2003/0095781 A1 | 5/2003 | Williams | |
| 2003/0097149 A1 | 5/2003 | Edwards et al. | |
| 2003/0191371 A1 | 10/2003 | Smith et al. | |
| 2003/0195392 A1 | 10/2003 | Hamel et al. | |
| 2003/0212333 A1 | 11/2003 | Rabiner et al. | |
| 2004/0024291 A1 | 2/2004 | Zinkel | |
| 2004/0049208 A1 | 3/2004 | Hill et al. | |
| 2004/0054322 A1 | 3/2004 | Vargas | |
| 2004/0059375 A1 | 3/2004 | Ginn et al. | |
| 2004/0068172 A1 | 4/2004 | Nowinski et al. | |
| 2004/0102804 A1 | 5/2004 | Chin | |
| 2004/0143167 A1 | 7/2004 | Branch et al. | |
| 2004/0143169 A1 | 7/2004 | Branch et al. | |
| 2004/0152955 A1* | 8/2004 | McGinley | A61B 17/1703 600/300 |
| 2004/0176801 A1 | 9/2004 | Edwards et al. | |
| 2004/0186346 A1 | 9/2004 | Smith et al. | |
| 2004/0215143 A1 | 10/2004 | Brady et al. | |
| 2004/0217069 A1 | 11/2004 | Columbus | |
| 2004/0220588 A1 | 11/2004 | Kermode et al. | |
| 2005/0043682 A1 | 2/2005 | Kucklick | |
| 2005/0065535 A1 | 3/2005 | Morris et al. | |
| 2005/0065543 A1 | 3/2005 | Kahle et al. | |
| 2005/0098932 A1 | 5/2005 | Panosian | |
| 2005/0107671 A1 | 5/2005 | McKinley | |
| 2005/0107820 A1 | 5/2005 | Forsberg et al. | |
| 2005/0143817 A1 | 6/2005 | Hunter et al. | |
| 2005/0159711 A1 | 7/2005 | Kathrani et al. | |
| 2005/0277829 A1 | 12/2005 | Tsonton et al. | |
| 2006/0135962 A1 | 6/2006 | Kick et al. | |
| 2006/0167357 A1 | 7/2006 | Lauritsch et al. | |
| 2006/0173245 A1 | 8/2006 | Todd et al. | |
| 2006/0224045 A1 | 10/2006 | Whipple et al. | |
| 2006/0247500 A1 | 11/2006 | Voegele et al. | |
| 2006/0253102 A1 | 11/2006 | Nance et al. | |
| 2006/0276871 A1 | 12/2006 | Amson et al. | |
| 2006/0287583 A1 | 12/2006 | Mangiardi | |
| 2007/0021743 A1 | 1/2007 | Rioux et al. | |
| 2007/0027456 A1 | 2/2007 | Gartner et al. | |
| 2007/0100210 A1 | 5/2007 | Selover et al. | |
| 2007/0100211 A1 | 5/2007 | Selover et al. | |
| 2007/0228753 A1 | 10/2007 | Dugal et al. | |
| 2007/0260273 A1 | 11/2007 | Cropper et al. | |
| 2007/0270898 A1 | 11/2007 | Lillehei | |
| 2007/0276191 A1 | 11/2007 | Selover et al. | |
| 2008/0103366 A1 | 5/2008 | Banchieri et al. | |
| 2008/0109026 A1 | 5/2008 | Kassam | |
| 2008/0125766 A1 | 5/2008 | Lubock et al. | |
| 2008/0132933 A1 | 6/2008 | Gerber | |
| 2008/0139928 A1 | 6/2008 | Lubock et al. | |
| 2008/0147018 A1 | 6/2008 | Squilla et al. | |
| 2008/0171934 A1 | 7/2008 | Greenan et al. | |
| 2008/0243162 A1 | 10/2008 | Shibata et al. | |
| 2008/0306490 A1 | 12/2008 | Lakin et al. | |
| 2008/0319268 A1 | 12/2008 | Michaeli et al. | |
| 2008/0319376 A1 | 12/2008 | Wilcox et al. | |
| 2009/0048622 A1 | 2/2009 | Wilson | |
| 2009/0062618 A1 | 3/2009 | Drew et al. | |
| 2009/0118587 A1 | 5/2009 | Voegele et al. | |
| 2009/0137877 A1 | 5/2009 | Minnelli et al. | |
| 2009/0192444 A1 | 7/2009 | Albrecht et al. | |

(56) References Cited

U.S. PATENT DOCUMENTS

| | | |
|---|---|---|
| 2009/0259097 A1 | 10/2009 | Thompson |
| 2009/0259106 A1 | 10/2009 | Catapano et al. |
| 2009/0281545 A1 | 11/2009 | Stubbs |
| 2009/0312611 A1 | 12/2009 | Mangiardi |
| 2009/0312783 A1 | 12/2009 | Whayne et al. |
| 2010/0010315 A1 | 1/2010 | Mangiardi |
| 2010/0029147 A1 | 2/2010 | Shrum et al. |
| 2010/0041949 A1 | 2/2010 | Tolkowsky |
| 2010/0081882 A1 | 4/2010 | Tess et al. |
| 2010/0130076 A1 | 5/2010 | Shrum et al. |
| 2010/0142215 A1 | 6/2010 | Waring |
| 2010/0188492 A1 | 7/2010 | Jacobsen et al. |
| 2010/0198346 A1 | 8/2010 | Keogh et al. |
| 2010/0274081 A1 | 10/2010 | Okoniewski |
| 2010/0284184 A1 | 11/2010 | Yang |
| 2010/0312064 A1 | 12/2010 | Weisenburgh et al. |
| 2010/0324488 A1 | 12/2010 | Smith |
| 2011/0005110 A1 | 1/2011 | Wieneke |
| 2011/0046449 A1 | 2/2011 | Minnelli et al. |
| 2011/0094204 A1 | 4/2011 | Bouillon et al. |
| 2011/0112360 A1 | 5/2011 | Swann et al. |
| 2011/0112375 A1 | 5/2011 | Bettuchi |
| 2011/0144443 A1 | 6/2011 | Shelton, IV et al. |
| 2011/0144590 A1 | 6/2011 | Sakai, Jr. et al. |
| 2011/0196204 A1 | 8/2011 | Setty et al. |
| 2011/0224742 A1 | 9/2011 | Weisel et al. |
| 2011/0301665 A1 | 12/2011 | Mercanzini et al. |
| 2011/0313286 A1 | 12/2011 | Whayne et al. |
| 2012/0010470 A1 | 1/2012 | Ducharme et al. |
| 2012/0029377 A1 | 2/2012 | Polak |
| 2012/0038293 A1 | 2/2012 | Guerrieri et al. |
| 2012/0071748 A1 | 3/2012 | Mark et al. |
| 2012/0109279 A1 | 5/2012 | Mayberry et al. |
| 2012/0123327 A1 | 5/2012 | Miller |
| 2012/0165611 A1 | 6/2012 | Warren et al. |
| 2012/0224375 A1 | 9/2012 | Zaderej et al. |
| 2012/0253353 A1 | 10/2012 | McBride |
| 2012/0253375 A1 | 10/2012 | Mark et al. |
| 2012/0289816 A1 | 11/2012 | Mark et al. |
| 2012/0310269 A1 | 12/2012 | Fearnot et al. |
| 2013/0044485 A1 | 2/2013 | Zaderej et al. |
| 2013/0058087 A1 | 3/2013 | Chang |
| 2013/0102851 A1 | 4/2013 | Mark et al. |
| 2013/0102886 A1 | 4/2013 | Mark et al. |
| 2013/0107508 A1 | 5/2013 | Rockrohr et al. |
| 2013/0188352 A1 | 7/2013 | Boyer et al. |
| 2013/0190571 A1 | 7/2013 | Chen et al. |
| 2013/0204095 A1 | 8/2013 | Mark et al. |
| 2013/0204287 A1 | 8/2013 | Mark et al. |
| 2013/0211202 A1 | 8/2013 | Perez-Cruet et al. |
| 2013/0241419 A1 | 9/2013 | Ghafoori et al. |
| 2013/0281791 A1 | 10/2013 | Aferzon |
| 2014/0029258 A1 | 1/2014 | Schroll et al. |
| 2014/0042083 A1 | 2/2014 | Mallard et al. |
| 2014/0126202 A1 | 5/2014 | Kachala |
| 2014/0134568 A1 | 5/2014 | Heinrich et al. |
| 2014/0142394 A1 | 5/2014 | Cataltepe |
| 2014/0142420 A1 | 5/2014 | Jackson, III |
| 2014/0171873 A1 | 6/2014 | Mark |
| 2014/0187922 A1 | 7/2014 | Mark et al. |
| 2014/0249371 A1 | 9/2014 | Fischvogt |
| 2014/0313766 A1 | 10/2014 | Krupa et al. |
| 2014/0378775 A1 | 12/2014 | Bowman et al. |
| 2015/0032022 A1 | 1/2015 | Stone et al. |
| 2015/0313631 A1 | 11/2015 | Fischvogt et al. |
| 2017/0367731 A1 | 12/2017 | Mark et al. |

FOREIGN PATENT DOCUMENTS

| | | |
|---|---|---|
| EP | 2770924 B1 | 5/2017 |
| GB | 2493165 A | 1/2013 |
| JP | 2000325356 A | 11/2000 |
| JP | 2001104323 A | 4/2001 |
| JP | 2002514448 A | 5/2002 |
| JP | 2006314744 A | 11/2006 |
| RU | 2009124446 A | 1/2011 |
| WO | 9958044 A1 | 11/1999 |
| WO | 03020140 A1 | 3/2003 |
| WO | 2006017507 A2 | 2/2006 |
| WO | 2006050047 A2 | 5/2006 |
| WO | 2007002251 A2 | 1/2007 |
| WO | 2007055983 A2 | 5/2007 |
| WO | 2007056010 A2 | 5/2007 |
| WO | 2008066543 A1 | 6/2008 |
| WO | 2008121294 A1 | 10/2008 |
| WO | 2009103759 A1 | 8/2009 |
| WO | 2013/063027 A1 | 5/2013 |

OTHER PUBLICATIONS

A. Schupak, "A Healthy Glow Florescent imaging helps surgeons cut more cancer cells," Poplar Science, Feb. 2011.

Modern Medicine, "New Device May Help Surgeons Resect Brain Tumors," "Fluorescence spectroscopy helps neurosurgeons identify hard-to-see tumor tissue," (Jan. 31, 2011).

Nader Sanal, MD, et al., "Intraoperative Confocal Microscopy for Brain Tumors: A Feasibility Analysis in Humans," www.neurosurgery-online.com (Jun. 2011).

Juan C. Fernandez-Miranda, M.D., et al. "High-definition fiber tracking guidance for intraparenchmyal endoscopic port surgery," J. Neurosurg/vol. 113/Nov. 2010.

Manuel Dujovny, et al., "Brain Retractor Systems," Neurological Research, vol. 37, No. 7, (2010).

T. Nakano, et al., "Endoscopic Treatment for Deep-seated or Multiple Intraparenchymal Tumoers: Technical Note," Dept. Of Neurosurgery, Hirosaki University Graduate School of Medicine. (2009).

Amin b. Kassam, et al., "Completely endoscopic resection of intraparenchymal brain tumors," J. Neurosurg./ vol. 110/ Jan. 2009.

K. Ogura, et al., "Neurosurgical Technique, New microsurgical technique for intraparenchymal lesions of the brain: transcylinder approach," Acta Neurochir (Wien)(2006).

Chun-Chung Chen, M.D., et al., "A stainless steel sheath for endoscopic surgery and its application in surgical evacuation of putaminal haemorrhage," Journal of Clinical Neuroscience (2005).

O. Barlas, et al., Clinical Article, "Stereotactically guided microsurgical removal of colloid cysts," Acta Neurochir (Wien) (2004).

Tetsuhiro Nishihara, M.D., et al., "A transparent sheath for endoscopic surgery and its application in surgical evacuation of spontaneous intracerebral hematomas," J. Neurosurg/vol. 92/Jun. 2000.

Donald M. O'Rourke, M.D., et al., "Vycor Medical, Inc.—Business Summary," www.vycormedical.com.

Non-Final Office Action dated Nov. 10, 2011 for U.S. Appl. No. 11/665,666.

PCT International Search Report dated Jun. 20, 2006 for PCT/US05/39185.

Wedeen, Van J., et al., "The Geometric Structure of the Brain Fiber Pathways," Science 335, 1628 (2012).

Office Action dated May 9, 2013 for U.S. Appl. No. 11/665,666.

PCT International Search Report & Opinion dated Apr. 9, 2013 for PCT/US2012/061568.

Response to Non-Final Office Action dated Nov. 10, 2011 for U.S. Appl. No. 11/665,666.

Final Office Action dated May 30, 2012 for U.S. Appl. No. 11/665,666.

Response to Final Office Action dated May 30, 2012 for U.S. Appl. No. 11/665,666.

PCT International Search Report and Written Opinion dated Sep. 21, 2015 for PCT/US2015/018573.

PCT International Search Report dated Jul. 24, 2014 for PCT/US2014/015755.

PCT International Search Report dated May 9, 2014 for PCT/US2014/015071.

Notice of Allowance dated Jul. 8, 2015 for U.S. Appl. No. 13/444,713.

Non-Final Office Action dated Mar. 20, 2015 for U.S. Appl. No. 13/444,713.

Interntational Search Report on Patentabiity dated 9//2016 for PCT/US2015/018573.

(56) References Cited

OTHER PUBLICATIONS

PCT Internatinal Search Report dated May 9, 2014 for PCT/US2014/015071.

* cited by examiner

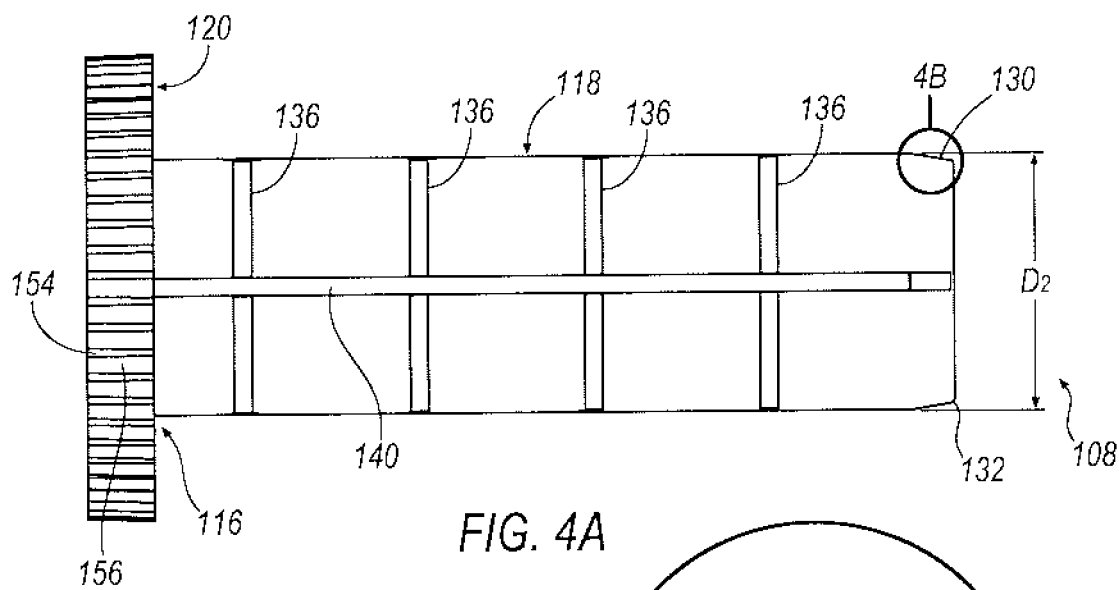
FIG. 4A
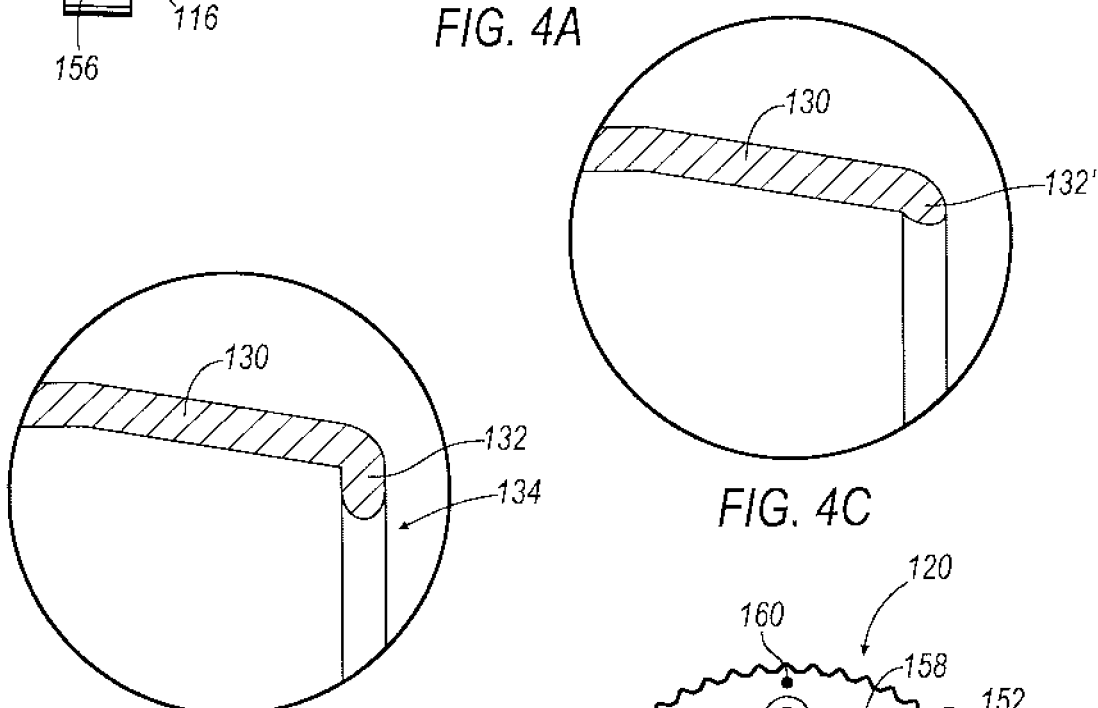
FIG. 4C
FIG. 4B
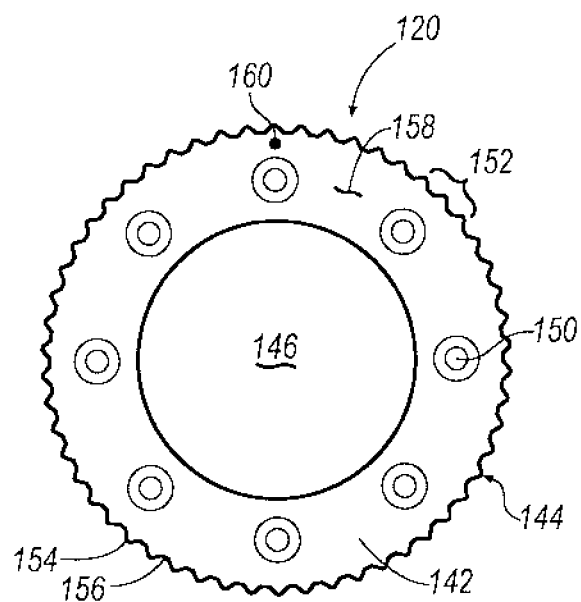
FIG. 5

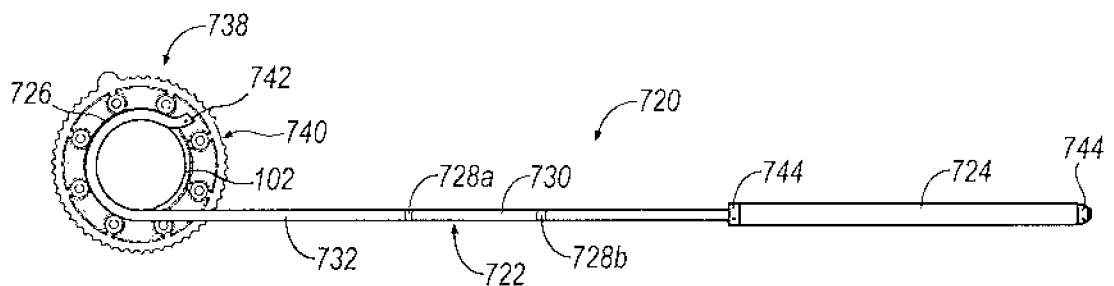
FIG. 19C
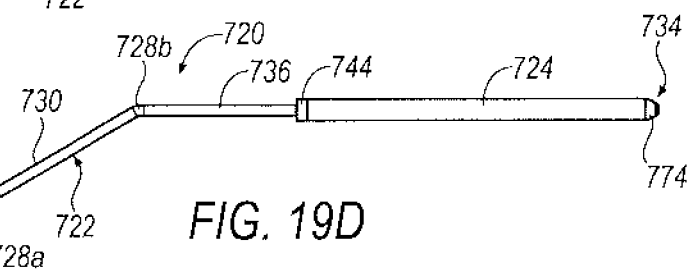
FIG. 19D
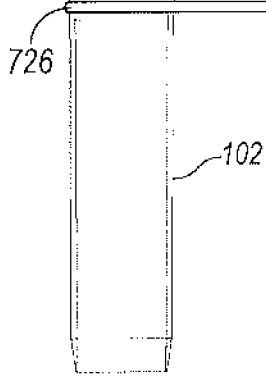
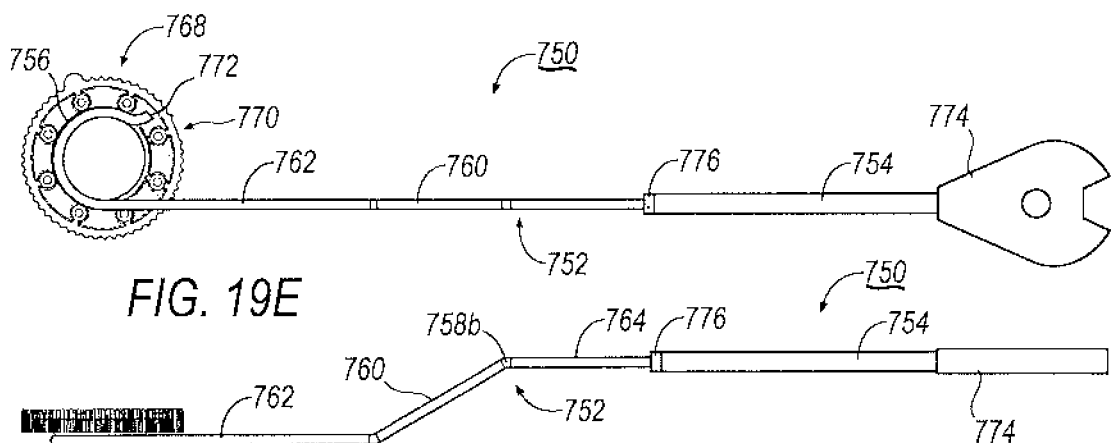
FIG. 19E
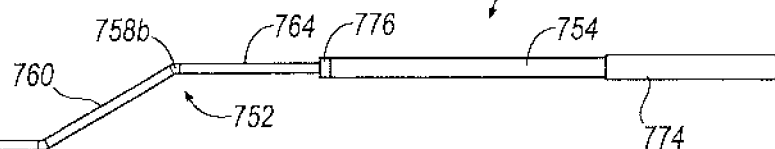
FIG. 19F
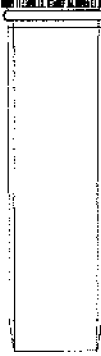

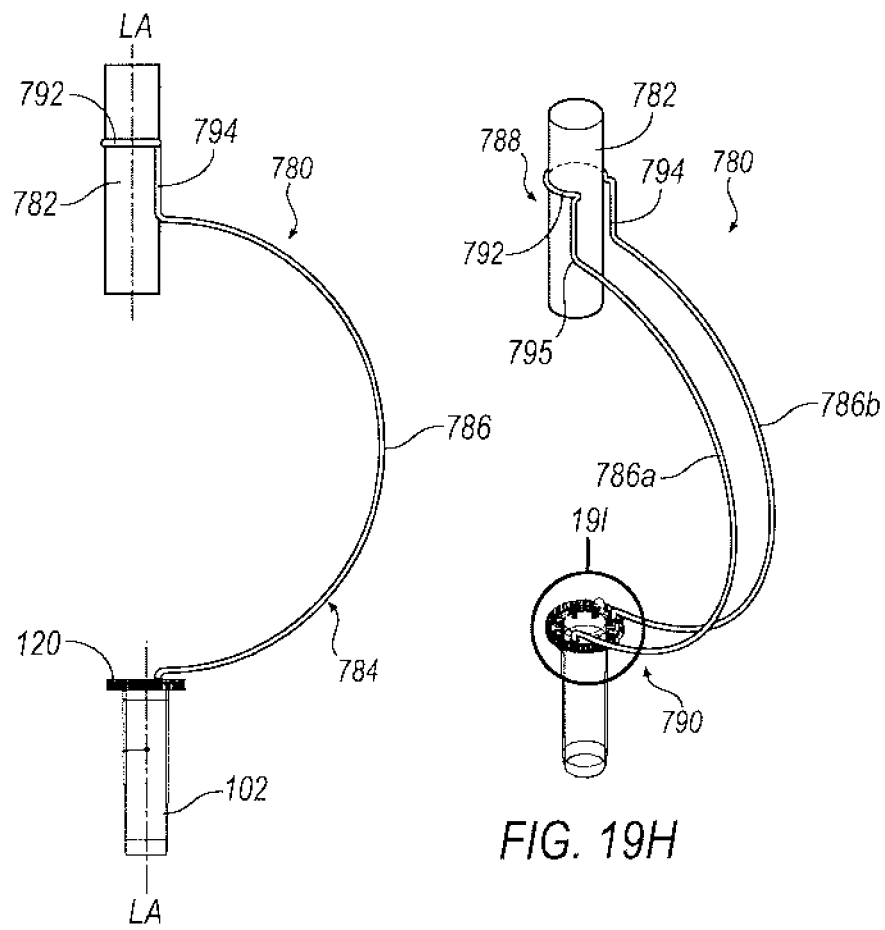
FIG. 19G
FIG. 19H
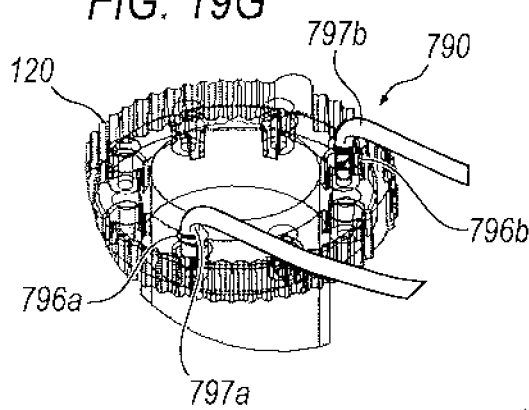
FIG. 19I
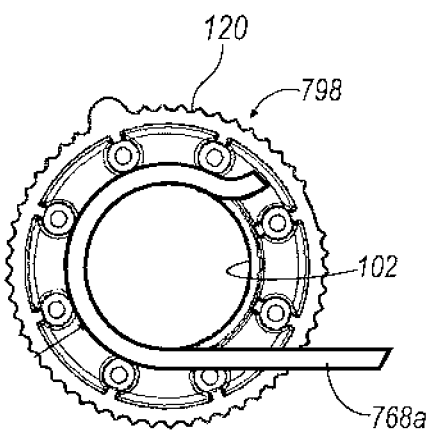
FIG. 19J

SURGICAL ACCESS ASSEMBLY AND METHOD OF USING SAME

CROSS-REFERENCE TO RELATED APPLICATIONS

This Application is a continuation of U.S. patent application Ser. No. 16/102,416 filed on Aug. 13, 2018, which application is a continuation of application Ser. No. 13/474,433 filed on May 17, 2012, now abandoned, which is a continuation-in-part of application Ser. No. 13/444,722 filed on Apr. 11, 2012, now U.S. Pat. No. 9,579,121, which is a continuation-in-part of application Ser. No. 13/444,713, filed on Apr. 11, 2012, now U.S. Pat. No. 9,186,175, which is a continuation-in-part of application Ser. No. 13/444,732, filed on Apr. 11, 2012, now U.S. Pat. No. 9,625,523, said application Ser. No. 13/444,713 is a continuation-in-part of application Ser. No. 13/280,015 filed on Oct. 24, 2011, now U.S. Pat. No. 9,770,261, which is a continuation-in-part of application Ser. No. 11/665,666 filed on Oct. 28, 2005, now abandoned, filed as application No. PCT/US05/39185 on Oct. 28, 2005. PCT/US05/39185 is a claims the benefit of application 60/623,094 filed on Oct. 28, 2004. The entire contents of these applications are incorporated herein by reference in their entirety.

TECHNICAL FIELD

The present disclosure relates generally to a surgical device for use with delicate and critical tissues, as well as methods of accessing and performing surgery using same. The present disclosure also relates to treatment of a surgical site.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration, hormonal and other metabolic functions, the diagnosis and treatment of disorders that are affected by abnormalities of the CNS and/or brain function presents unique challenges not encountered elsewhere in the body.

For example, abnormalities such as intracranial cerebral hematomas (ICH), abscesses, glioblastomas (GB), and metastases (mets) manifest themselves in the intraparenchymal subcortical space (i.e., the white matter) of the brain are particularly challenging to access, let alone treat. Similarly, functional diseases/abnormalities, such as, for example, Alzheimer's, Parkinson's, epilepsy, bi-polar, depression, which also have origins in hard to access areas of the brain, are also difficult to access and subsequently treat. Central nervous system ("CNS") based disease/abnormalities, and metabolic/regulatory systemic conditions that result, for example, obesity, hormone regulated conditions, insulin production and subsequent flow/perfusion into the body, etc., also have root causes within the brain, as do addictions and the recognition of and response to pain stimulus. Indeed, the location to access the area in the brain where the functional diseases/abnormalities, CNS based disease/abnormalities, metabolic/regulatory systemic conditions, and pain recognition, is difficult to reach, or even apply therapy thereto. For example, the hemispheres of the brain contain eloquent communication structures (neural network) which are located in the subcortical space, called fiber tracts and fascicles. Thus, traditionally, unless the condition that the patient was experiencing was considered anything but "superficial," and not near eloquent structures of the brain, have been considered challenging to access, simply because of the biological cost of surgical access to the abnormality are considered too high and may be just as damaging as letting the condition take its course. Similarly, tissue abnormalities such as tumors, cysts and fibrous membrane growths which manifest within the intraventricular space of the brain are considered challenging to safely access and often inoperable, due to their size or location within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating on the brain so as not to disturb delicate blood vessels and nerves to prevent adverse consequences resulting from a surgical intervention.

Traditionally, accessing areas of the brain where abnormalities or other conditions which manifest in deeper spaces within the brain has meant a need for a surgery that creates a highly invasive approach, if any approach at all is feasible. In some instances, in order to obtain access to target tissue, a substantial portion of the skull is removed and entire sections of the brain are retracted or removed to obtain access. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary. These approaches are referred to as Expanded Endonasal Approaches (EEA) and were pioneered by one of the inventors of this disclosure.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance (IGS—Image guided surgery), in which an image of the navigation probe or navigated surgical instrument is superimposed on a pre-operative image to demonstrate the location of the instrument to the surgeon and trajectory of further movement of the probe or instrument while in the surgical suite.

In recent years, surgical access systems have been developed to provide access to previously difficult to access areas. One such prior art system is shown in FIGS. 1A-1C. System 10 includes a retractor 20 and an introducer 40. Introducer 40 includes a cone-shaped distal end 42 with an opening 52 therein (best seen in FIG. 1C). The cone-shaped distal end is configured to be a generally blunt, flat surface. With introducer 40 positioned within retractor 10, system 10 is inserted into brain tissue, thereby pushing brain tissue away while providing access to an area of interest. Once system 10 is delivered to the area of interest, retractor 10 is rigidly fixed in position. More specifically, retractor 10 is fixed in space with the use of a standard or conventional neurosurgical fixation device. Once, retractor 10 is fixed in place, introducer 40 is then removed from retractor 10, while leaving retractor 10 in its fixed place, thereby creating a pathway through the brain tissue.

While access system 10 may provide a manner to access certain brain tissue, the blunt shaped distal end of can actually cause transient or even permanent deformation and trauma of delicate tissue structures which can manifest itself in temporary or permanent neurological deficits after surgical cytoreduction due to damage of blood vessels, cranial nerves, fiber tracts and fascicles. Opening 52 may cause coring of tissue, also leading to damage of the tissues and structures as introducer 40 is pushed through tissue. Further, by rigidly fixing the placement of retractor 10, manipulation of retractor 10 is impeded and requires constant attention by loosening and retightening to re-position for even micro-movement of the retractor 10, thereby lengthening procedure time.

Another issue that needs to be addressed is visibility. Typically when employing an access system in a surgical procedure, it is often like operating in a poorly lit tunnel. To provide illumination, it is known to place a light source within the introducer sheath, such as an endoscope. However, when using an endoscope, the light source takes up a significant amount of working space within the introducer sheath, thus reducing the functional working area for other instruments, as well as minimizing the ability to move other instruments within the surgical site.

Alternatively, light must be delivered from a remote or external location, such as a microscope or exoscope. However, in the case of microscopes and exoscopes, the external light source is often blocked by the surgeon and/or instruments in the surgical field. At a minimum, the effectiveness is greatly diminished at the distal end of the introducer sheath where the actual surgical work and/or treatment is occurring, and where effective visualization is needed the most.

Notwithstanding the foregoing advances in imaging technology and both frame and frameless stereotactic image guidance techniques, there remains a need for improved surgical techniques and apparatus for operating on brain tissue.

There also exists a need for improved and effective treatment regimens and options. Traditionally, once a disease or medical condition is identified, patients are treated with a "one-size" fits all approach which typically includes a generic protocol regimen which is delivered systemically, thereby affecting the entire body unnecessarily. For example for certain cancers a heavy chemotherapy protocol regimen is delivered systemically and is designed to provide a balance between enough poison to kill the cancerous cells and tissue without killing the healthy tissues. High doses and multiple exposures to radiation are also typically used and delivered by products such as the Gamma Knife and Cyber Knife. However, such treatment regimens are often nothing more than a series of "experiments" on the patient in an effort to find an effective treatment plan. Accordingly the patient must be monitored to ascertain the effectiveness of the generic therapeutic regimen and continuous modification and tweaking of the treatment regime is performed based upon the positive or negative results of each of the previous successes or failures while attempting to balance the sparing of healthy tissues and poisoning effect of the treatment process on the whole patient. Such a treatment regime effectively results in the patient being a guinea pig until a treatment regime is achieved to manage the disease or as in most cases of brain cancers the patient dies from the disease. Unfortunately, in the case of brain cancers, the patient often succumbs to the disease before an effective treatment regime is achieved. Regardless of these heroic clinical efforts that are very biologically caustic to the patient, rarely are any of the current treatment paradigm curative. In fact, since patients diagnosed with brain cancers often do not typically live beyond 9-14 months after initial diagnosis of the disease, long term clinical implications of whole body chemo or target directed radiation therapy are unknown in these patients and may be detrimental if the patient lived long enough for the true impact to be understood.

In addition, most current therapeutic treatment regimens that involve delivering therapy regimens systemically and depend on overcoming the limitations of delivery through the bloodstream which include the filtering effects of the liver and kidneys. However, the blood-brain barrier, which serves to separate circulating blood from the brain extracellular fluid in the central nervous system (CNS), creates additional challenges to delivering therapeutic agents to specific regions of the brain through the bloodstream. More specifically, the blood-brain barrier actually functions in a neuroprotective role. Thus the blood-brain barrier actually impedes delivery of therapeutic agents to the brain. Therapeutic molecules that might otherwise be effective in therapy are typically larger molecules than the blood brain barrier sieve and for this reason do not cross the blood brain barrier in adequate amounts. In addition to the blood brain barrier, other mechanisms exist within the body to filter out foreign materials and chemicals such as the liver and the kidneys. These filtering create additional challenges for the delivery of appropriate concentrations of therapeutics the intended site of treatment for central nervous system diseases and other hormonally based abnormality/diseases that call for regulation of bodily functions and activities as well as pain modulation.

To overcome the treatment issues associated with the blood brain barrier, mechanical opening of the blood brain barrier has been proposed, which may complicate the procedure. In addition, use of smaller particles (i.e., nanoparticles) have been proposed, whereby the smaller particles are sized to pass through the blood brain barrier, then are attempted to be recombined to form a larger and more effective therapeutic molecule. However, in some instances, the smaller particles fail to recombine in therapeutic levels. Other means to breach the blood brain barrier include delivering chemicals designed to temporarily open up the blood brain barrier to allow for a period of time that larger molecules at therapeutic levels may pass across it. Once across the blood brain barrier, the therapeutic treatment must still get to the diseased tissue, resulting in poisoning healthy tissue, as well as diseased tissue.

Additionally, it is believed that since certain diseases of the brain, such as cancers, often behave like a virus or bacteria in that once they are treated, but not eradicated by the therapeutic regimen delivered to them, they may morph and become resistant to the treatment that had been previously delivered to them. These residual unaffected abnormal cells may mutate into a strain of cells that become resistant to the therapy that was delivered to them previously. In cases of functional diseases, and/or other abnormalities, the effectiveness of treatment on brain tissue may be difficult to evaluate.

Accordingly, there exists a need for effective treatment regimes that overcomes the challenges created by systemic delivery of therapies so as to overcome the filtering effects of the kidneys, liver and blood brain barrier, while providing targeted treatment to the diseased tissue, dysfunctional tissue, or brain abnormality rather than healthy tissue. There also exists a need for a method of evaluating effectiveness of previously delivered treatment, as well as providing for subsequent therapy/treatment.

BRIEF DESCRIPTION OF THE DRAWINGS

Exemplary embodiments of the present disclosure will now be described in greater detail with reference to the attached figures, in which:

FIG. 4A is a side elevational view of the outer sheath of FIG. 3.

FIG. 4B is an enlarged cross-sectional view of a portion of the distal end of the outer sheath of FIG. 4A.

FIG. 4C is an enlarged cross-sectional view of a portion of an alternative embodiment of the distal end of the outer sheath of FIG. 4A.

FIG. 5 is an end view of outer sheath of FIG. 3.

FIG. 19C is a top view of the outer sheath operatively connected to a first exemplary arrangement of a holding arrangement therefore.

FIG. 19D is an elevational view of the outer sheath and holding arrangement of FIG. 19C.

FIG. 19E is a top view of the outer sheath operatively connected to a second exemplary arrangement of a holding arrangement therefore.

FIG. 19F is an elevational view of the outer sheath and holding arrangement of FIG. 19C.

FIG. 19G is a side elevational view of the outer sheath operatively connected to a third exemplary arrangement of a holding arrangement therefore and an exoscope.

FIG. 19H is a perspective elevational view of the outer sheath, holding arrangement and exoscope of FIG. 19G.

FIG. 19I is an enlarged perspective view of a top portion of the outer sheath, illustrating the connection of the holding arrangement to the outer sheath.

FIG. 19J is a top view of the top portion of the outer sheath, illustrating an alternative connection of the holding arrangement of FIGS. 19G-H.

DETAILED DESCRIPTION

Figure 1A:
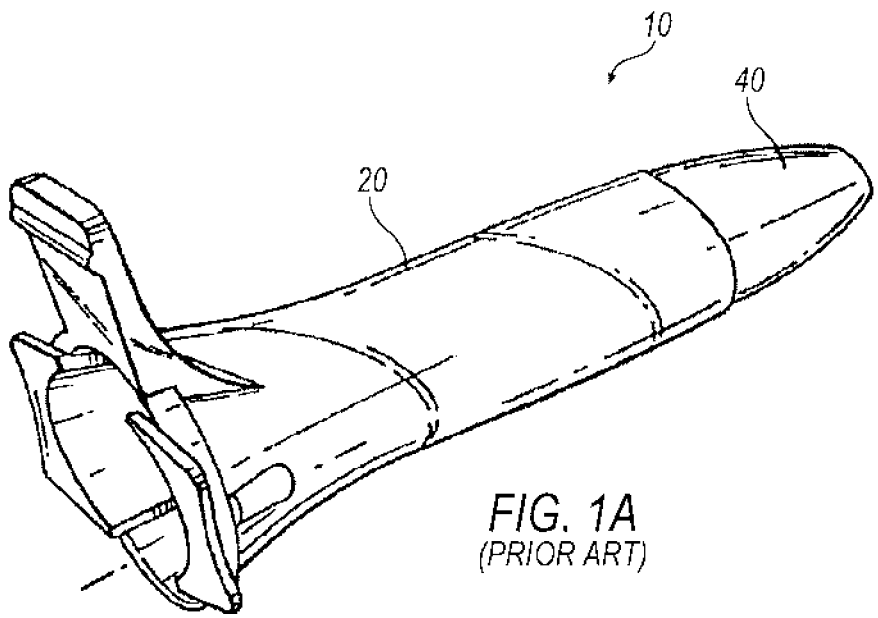
FIGS. 1A-1C illustrate a prior art surgical access system.
Figure 1B:
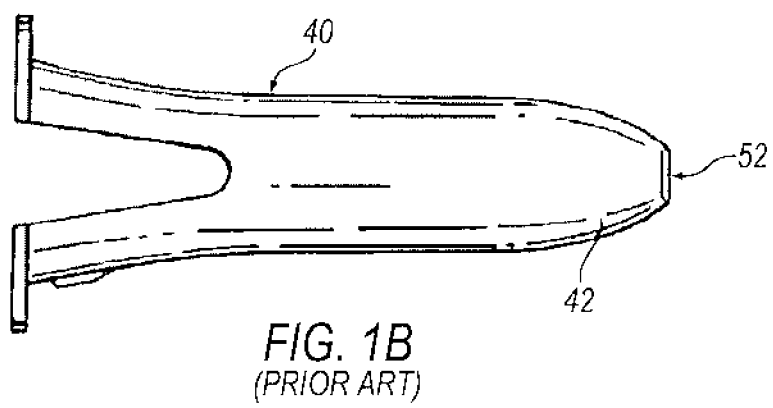

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens.

Figure 2:
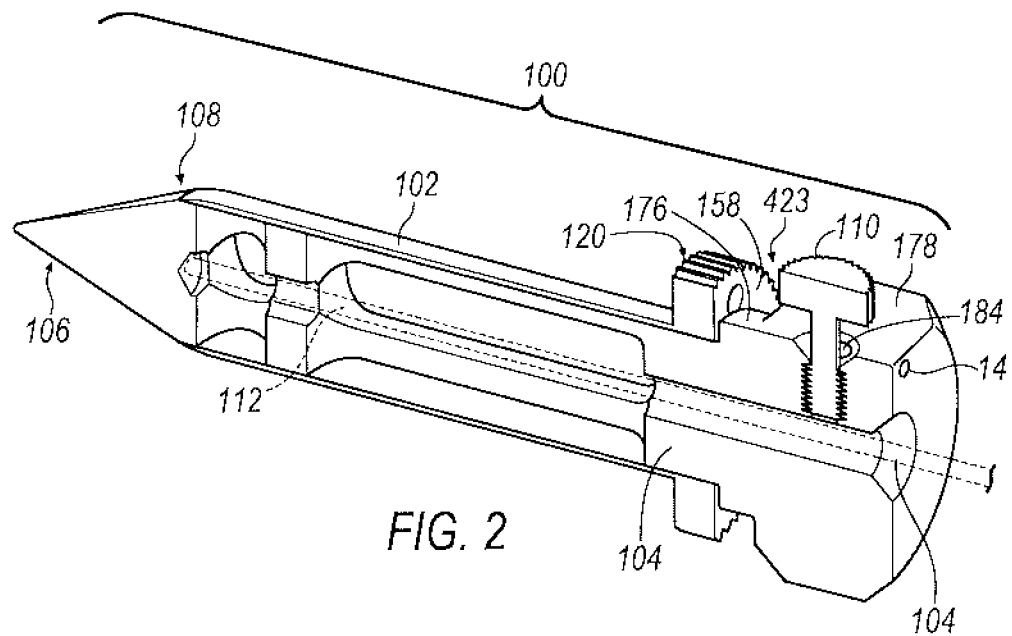
FIG. 2 is a perspective cross-sectional view of an exemplary arrangement of a surgical access assembly.

Referring to FIG. 2, a perspective cross-sectional view of a surgical access assembly 100 is shown. In one exemplary arrangement, surgical access assembly 100 comprises a hollow outer sheath 102 and a selectively removable obturator 104. As best seen in FIG. 2, obturator 104 is configured with a length that is longer than a length of outer sheath 102 such that a distal end 106 of obturator 104 protrudes a predetermined distance from a distal end 108 outer sheath 102, as will be discussed below in greater detail.

A locking member 110 may also be provided. Locking member 100 is configured to operatively retain a separate navigation member 112 (shown in phantom) within obturator 104, as will be discussed in greater detail below. A retaining member 114 may be secured within a portion of obturator 104 to prevent locking member 110 from being completely disengaged from obturator 104.

Figure 3:
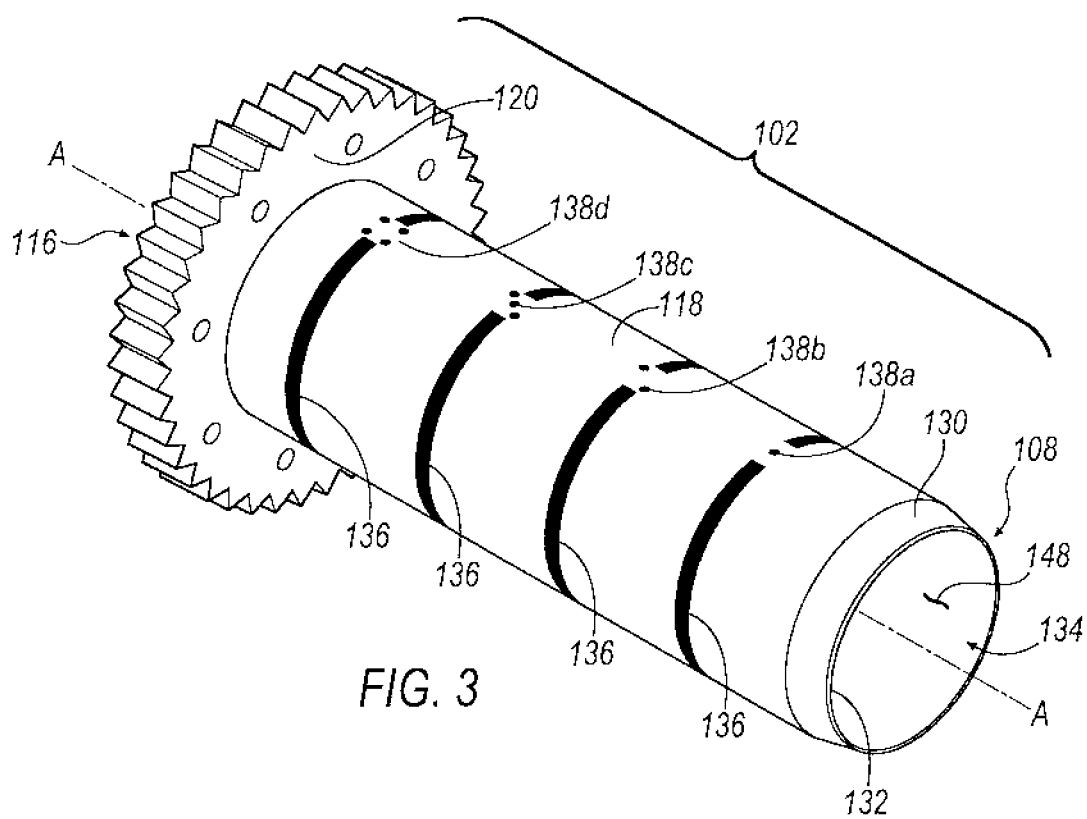
FIG. 3 is a perspective view of an outer sheath of the surgical access assembly of FIG. 2.

Referring now to FIGS. 3-5, outer sheath 102 will be described in greater detail. Outer sheath 102 is defined by distal end 108 and a proximal end 116 and includes a generally hollow body portion 118 and a grip portion 120. In one exemplary arrangement, grip portion 120 is configured as a ring, as illustrated in the drawings. However, it is understood that grip portion 120 need not be configured as a ring. For ease of explanation, grip portion 120 will be referred to hereinafter as grip ring 120. Grip ring 120 is fixedly secured to body portion 118 at proximal end 116. In one exemplary arrangement, body portion 118 is constructed of a clear biocompatible material that permits viewing of normal tissue, abnormal tissue, as well as critical structures that are disposed outside of body portion 118 when outer sheath 102 is disposed within such tissue. In one exemplary arrangement, outer sheath 102 is constructed of polycarbonate, though other biocompatible materials may be employed, including resins.

In one exemplary configuration, an imaging mechanism may be incorporated into outer sheath 102 that would permit visualization of tumors, vessels, fiber tracks, fascicles and even healthy tissue, in real-time. Indeed, as will be explained in further detail below, the imaging mechanism will enable physiological functional imaging to provide information about the characteristics of the cortical fiber tracks to be visible, thereby enabling a user to separate and park such fibers on either side of outer sheath 102 rather than cutting, stretching and potentially damaging such fibers while gaining access to a desired location within the brain. Further, as will be explained in further detail below, the imaging mechanism may also enable the surgeon to have real-time information about the fiber tract and fascicle location, after placement of outer sheath 104, and during abnormality resection procedure therethrough. In addition to white matter tract imaging, mapping of the characteristics of the cerebral blood flow may be obtained.

In one exemplary embodiment, the imaging mechanism may be an ultrasound probe incorporated into outer sheath 102. For example, outer sheath 102 may be provided with one or more channels within the wall that defines outer sheath 102 that are configured with one or more small diameter ultrasound probes. In another arrangement, a single ultrasound probe that is configured to be received within outer sheath 102 may be provided. In yet another embodiment, a low field MRI probe may be selectively placed in outer sheath 102 to provide enhanced imaging. In yet another embodiment a low field MRI imaging coil may be molded into or bonded into outer sheath 102. In still another exemplary arrangement, the probe may be an optical coherent tomography (OCT) imaging or spectroscopy.

In another exemplary arrangement, as will be explained in further detail below, outer sheath 102 may also be (or alternatively be) provided navigational capabilities that permit a user to "read" the location of outer shaft 102 after placement at an area of interest, as well as update the location of outer sheath 102 during a procedure. In one exemplary arrangement, an RFID chip or sensor that is configured to be tracked by a navigation system, may be incorporated into outer sheath 102. For example, an RFID chip or sensor may be permanently attached to outer sheath 102, for example, by impregnating or molding the RFID chip or sensor therein. In other exemplary arrangements, a temporary sensor or chip may be incorporated into or attached to outer sheath 102. For example, outer sheath 102 may be provided with one or more channels within the wall that defines outer sheath 102. An RFID chip and/or sensor may be positioned within the channels.

Distal end 108 of outer sheath 102 may be configured with a tapered portion 130 that extends towards a center axis A-A of outer sheath 102 to a distal edge 132 that surrounds an opening 134 in distal end 108 of outer sheath 102. Tapered portion 130 serves to ease the transition between outer sheath 102 and a distal tip portion 172, without drag, trauma or coring of tissue from a diameter that defines a body portion 168 of obturator 104 to a diameter that defines body portion 118 of outer sheath 102. In one exemplary configuration, distal end 108 may be configured with a radius or other configuration so as to create a smooth/atraumatic transition of the brain tissue when surgical access assembly 100 is inserted into the brain.

Figure 1C:
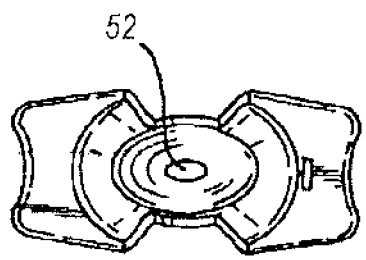

For example, as best seen in FIG. 4B, distal edge 132 is configured so as to be non-sharpened and radiused. In one exemplary arrangement, distal edge 132 is configured as a 0.3 mm diameter radiused rim. Tapered portion 130 and radiused distal tip 132 cooperates with obturator 104 to atraumatically move tissue, as well as various structures within the brain, including white matter, away from outer sheath 102 without cutting tissue or such structures. Indeed, unlike prior art devices that include either a blunt tip distal end or a tapered leading edge such as that shown in FIG. 1C, radiused distal tip 132 cooperates with tapered portion 130 and obturator 104 to prevent bruising and damage to various tissue. More specifically, this configuration facilitates entry of outer sheath 102 into delicate tissue, but without cutting such delicate tissue. Insertion of surgical access assembly 100 will be explained in further detail below.

Body portion 118 may further be provided with a plurality of spaced apart indicators 136. Indicators 136 generally extend about the circumference of body portion 118 and each may further incorporate a secondary indicator 138 that visually illustrates a predetermined location on body portion 118, as shown in FIG. 3. While FIG. 3 illustrates four indicators 136, it is understood that body portion 118 may be provided in a variety of lengths and that any number of indicators 136 may be provided. Body portion 118 may also be provided with a longitudinal indicator 140. More specifically, as best seen in FIG. 4A, longitudinal indicator 140 extends from proximal end 116 to distal end 108. Indicators 136, 138 and 140 may be printed onto either an internal or external surface of body portion 118 with an imaging visible ink such as, for example ink containing fluro-deoxyglucose (FDG), Technicium 99, Gadolinium, titanium dust, barium sulfate, a combination of the above or other suitable imaging material. Indicators 136 and 138 provide a reference point for the operator of system 100, as structures may be visible through body portion 118. Indicator 136, 138 and 140 may also be configured to be visible under MRI, CT, PET, or any other suitable imaging modality to enable easy identification of areas of interest. In one alternative embodiment, indicators 136, 138 and/or 140 may be etched or printed onto body portion 118, either on the internal or external surface of body portion 118.

Details of grip ring 120 are best seen in FIG. 5. Grip ring 120 is generally configured as a flange member 142 defined by an outer periphery 144 and an inner opening 146. Inner opening 146 may be sized to generally correspond to the diameter of a lumen 148 defined by body portion 118. Outer periphery 144 is sized to have a diameter that is larger than lumen 148 of body portion 26. Flange member 142 may further be provided with one or more small openings 150 that are disposed therein. In one exemplary arrangement, a plurality of small openings 150 are provided that are spaced generally equi-distantly about inner opening 146. Small openings 150 will be described in further detail below. Outer periphery 144 may further be provided with a textured surface 152 to provide for ease of gripping outer sheath 102. For example, in one exemplary arrangement, textured surface 152 comprises a plurality of alternating ridges 154 and grooves 156. However, it is understood that other textured surfaces may be employed.

Disposed on a proximal end surface 158 of flange member 142, an alignment feature 160 may be employed. Alignment feature 160 is used to indicate the location of longitudinal indicator 140 when outer sheath 102 is positioned within the brain. Alignment feature 160 will be discussed below in greater detail.

Figure 6A:
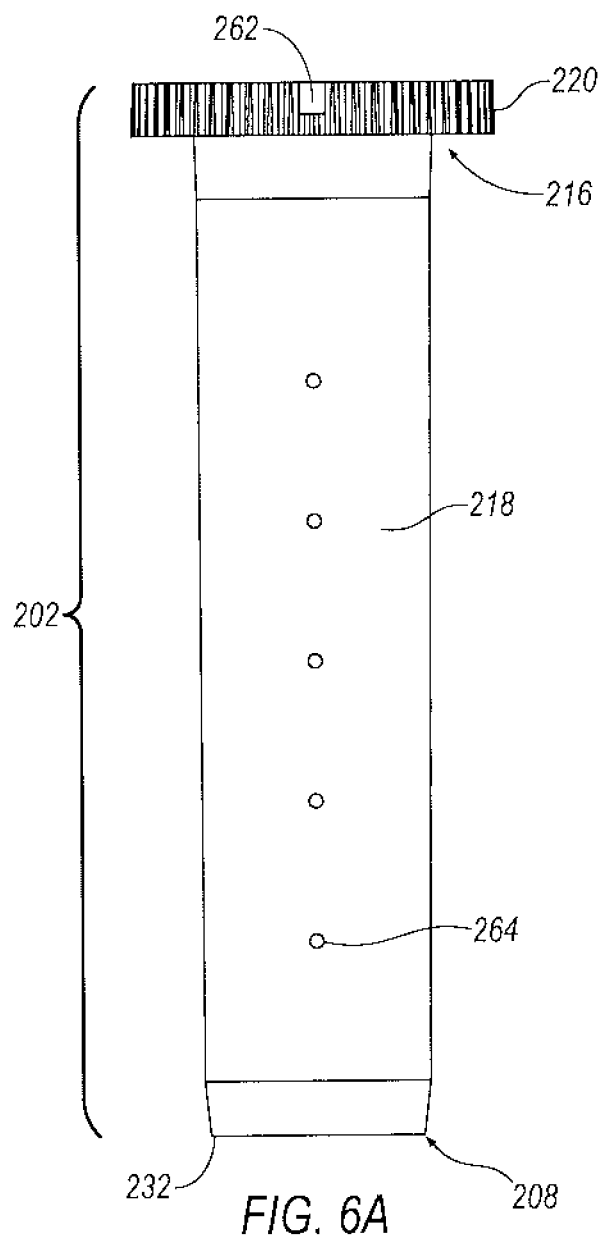
FIG. 6A is an elevational view of an alternative embodiment of an outer sheath.
Figure 6B:
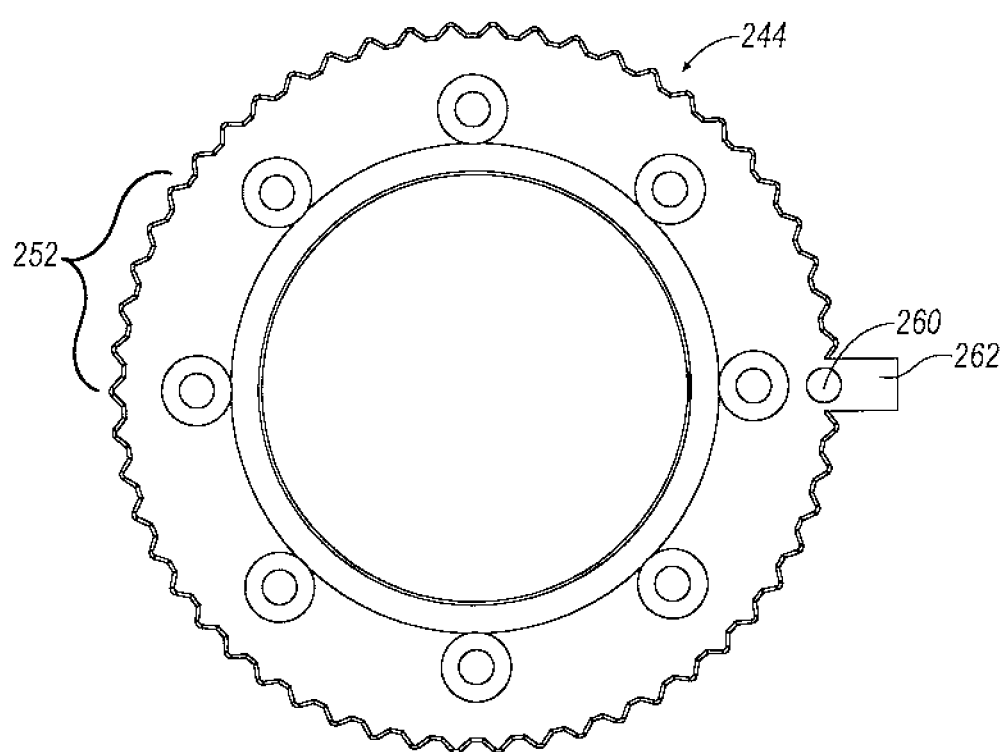
FIG. 6B is an end view of the outer sheath of FIG. 6A.

An alternative embodiment of outer sheath 202 is shown in FIGS. 6A-6B. Outer sheath 202 is similar to outer sheath 102 in that it is defined by a distal end 208, a proximal end 216 and a body portion 218. A distal edge 232 is generally configured to be similar as distal tip 132. A grip ring 220 is fixedly secured to body portion 218.

Figure 11A:
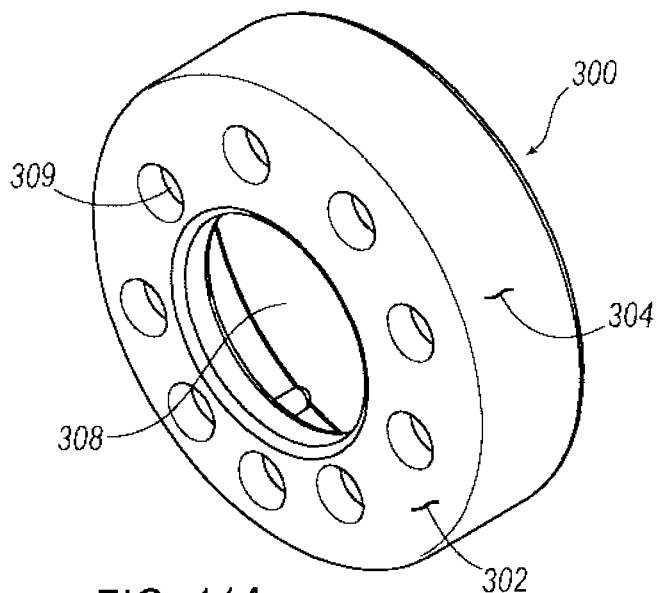
FIG. 11A is a perspective view of an illuminating ring that operatively connects to an outer sheath of the surgical access assembly.
Figure 11B:
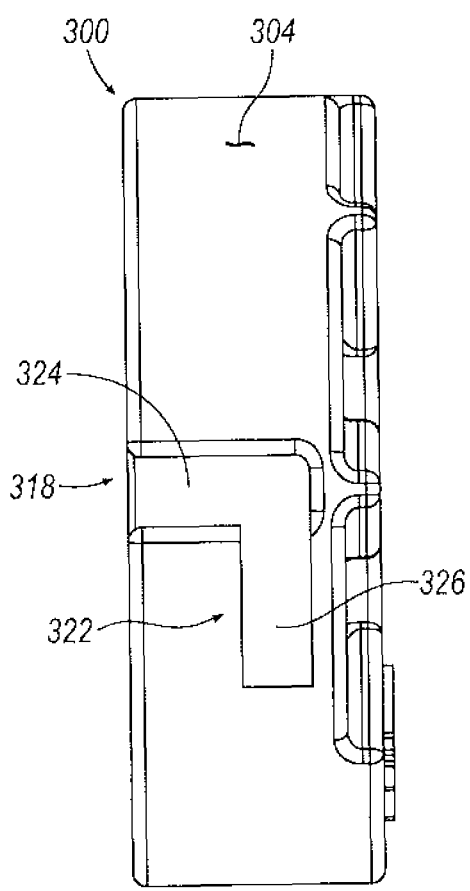
FIG. 11B is a side view of the illuminating ring of FIG. 11A.
Figure 11C:
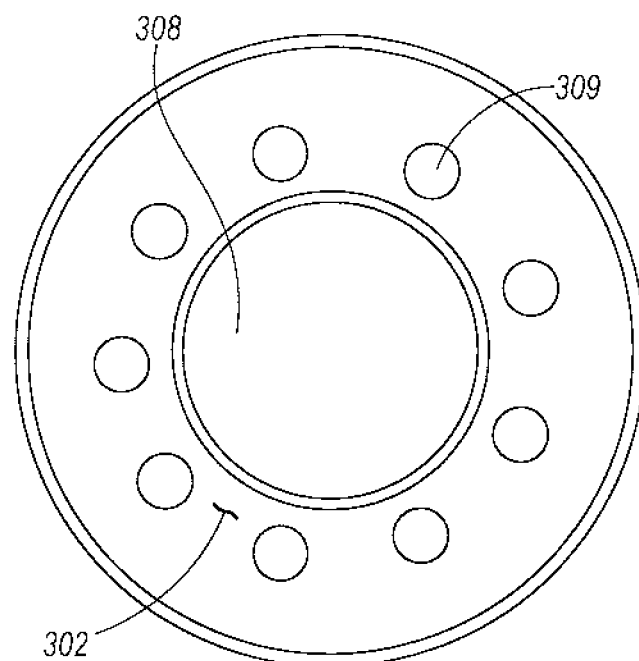
FIG. 11C is a top view of the illuminating ring of FIG. 11A.
Figure 11D:
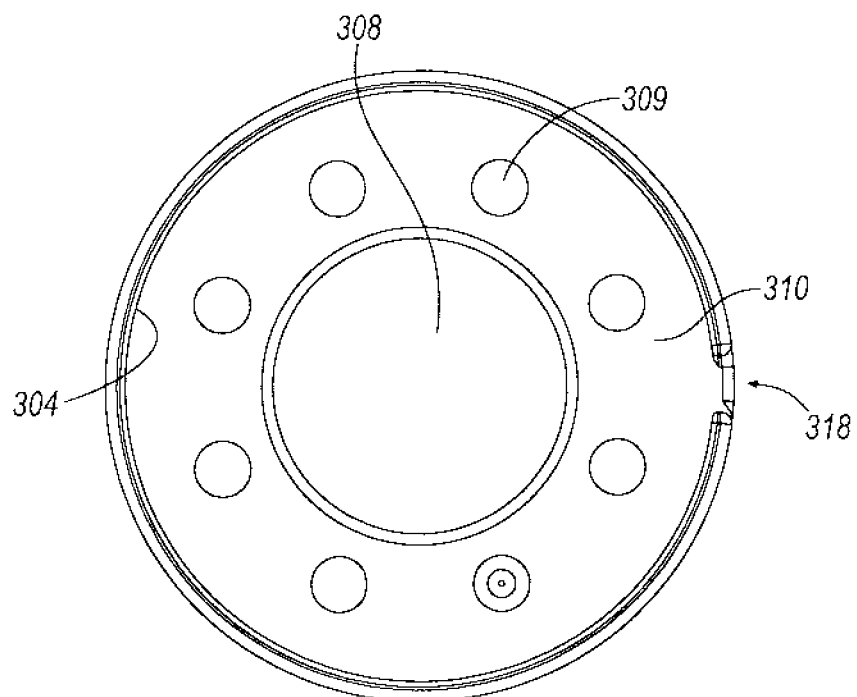
FIG. 11D is a bottom plan view of the illuminating ring of FIG. 11A.
Figure 11E:
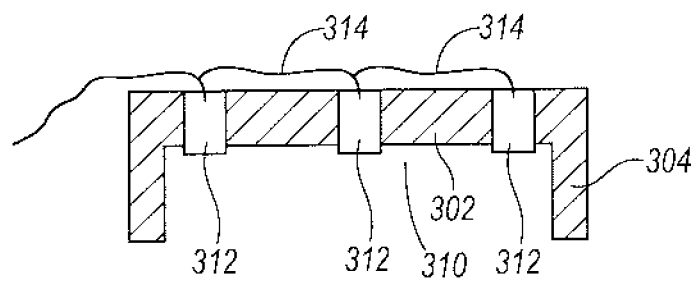
FIG. 11E is a cross-sectional view of an exemplary arrangement of a lighting arrangement for the illuminating of FIG. 11A.
Figure 11F:
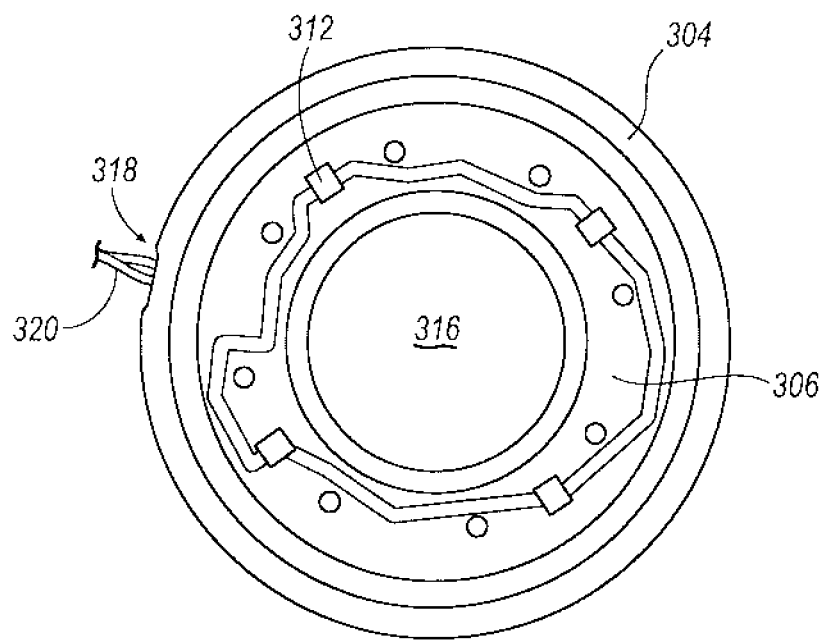
FIG. 11F is a plan view of a circuit board for use with the illuminating ring of 11A.

Grip ring 220 also includes a textured surface 252. Grip ring 220 further includes a locating member 262. Locating member 262 is configured to operatively connect an illumination ring (best seen in FIG. 11A) 300 to outer sheath 102. As may be seen, in one exemplary configuration, locating member 262 extends outwardly from outer periphery 244 of grip ring 220. Locating member 262 may also serve as an alignment feature for indicating the location of longitudinal indicator 240. Alternatively, a separate alignment feature 260 may be provided. For example, in FIG. 6B, alignment feature 260 is positioned adjacent locating member 262.

Body portion 218 may also be provided with indicators 34, 36, and 38 to assist in locating outer sheath 202 in operation. However, in another alternative arrangement, body portion 218 may be provided with indicators 264 that produce a signal void or minimal artifact under certain imaging modalities. In one specific arrangement, indicators 264 may be configured as small holes that are spaced apart at predetermined distances, as shown in FIG. 6A. In yet another alternative arrangement, indicators 264 may be configured as non-through divots. In still a further alternative arrangement, indicators 264 may be configured as a longitudinal groove (not shown) on either the internal or external surface of body portion 218.

Referring to FIGS. 7-10, obturator 104 will now be described. Obturator 104 is defined by distal end 106, a proximal end 166, a body portion 168 and a handle portion 170. Distal end 106 is configured with a generally conical shaped distal tip portion 172 that tapers to a tip member 174 to provide atraumatic dilation of tissue. In one exemplary arrangement, tip portion 172 tapers toward a closed tip member 174 so as to prevent coring of tissue as obturator 104 is inserted into the brain.

There are a number of variables that play the selection of the angle α that defines the taper of tip portion 172. These variables include the size of an outer diameter D1 of obturator 104, the desired length that distal tip portion 172 extends from body portion 168, and the desired offset for a distal tip of navigation member 112 and tip member 174. More specifically, it is contemplated that surgical access assembly 100 will be provided as part of a kit that may include multiple sized outer sheaths 102 and obturators 104, to provide the surgeon with a choice of different diameter sizes and lengths so as to provide flexibility for accessing areas of interest within the brain. However, to insure that the distal tip 174 is determinable regardless of which size diameter D1 of obturator 104 is used, taper angle α may be selectively adjusted. For embodiments that utilize navigation member 112 that positions a distal end thereof at a set position within obturator 104 (as will be explained in further detail below), to maintain an identical offset length between the distal end of navigation member 112 and distal tip 174 in different diameter D1 sized obturators 104, taper angle α will need to be increased, as diameter D1 increases.

For example, if diameter D1 of obturator 104 is 13.5 mm, an exemplary angle α may be 45.5° to provide effective atraumatic dilation, as well as a determinable distal tip 174 location. However, if diameter D1 of obturator 104 is 15.5 mm, an exemplary angle α' may be 52.8°.

Figure 8A:
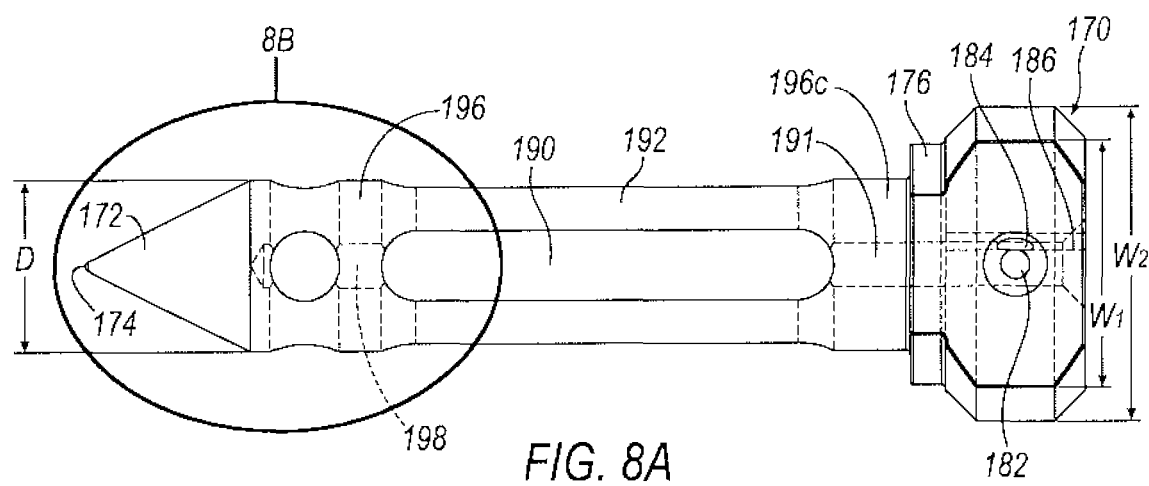
FIG. 8A is a top view of the obturator assembly of FIG. 7A.
Figure 8B:
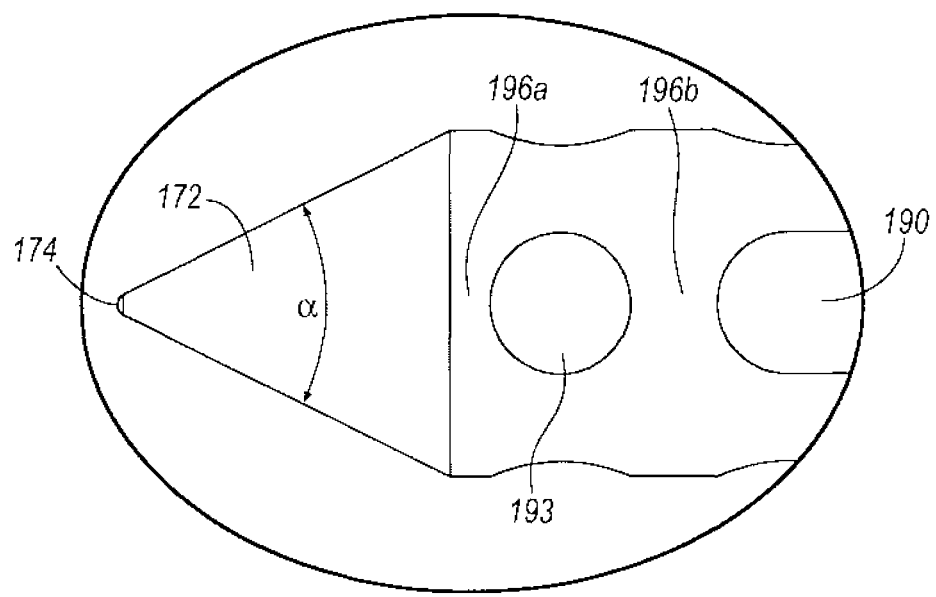
FIG. 8B is an enlarged view of a distal end of the obturator assembly taken from area 8B of FIG. 8A.
Figure 8C:
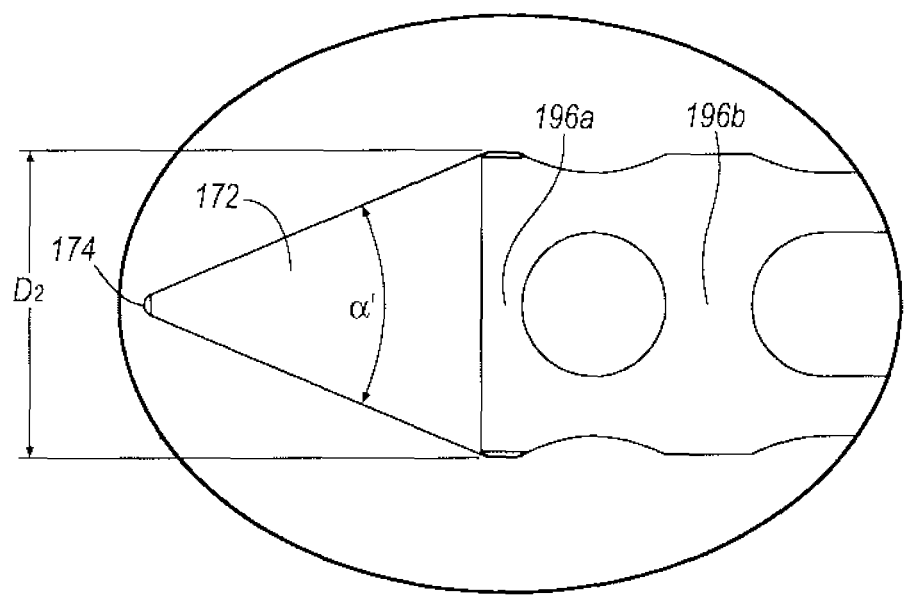
FIG. 8C is an alternative embodiment of the distal end of the obturator assembly taken from area 8B of FIG. 8A.

As best seen in FIG. 8B, distal tip 174 is configured to be radiused such that tip member 174 is rounded, and neither blunt, nor sharp. More specifically, tip member 174 is configured so as not to have any flat portions which during insertion can stretch or even tear the delicate tissues such as the vessels, fiber tracts and fascicles found in the brain. Further, because tip member 174 is closed, damage of such delicate tissues and fascicles are also avoided. In one exemplary embodiment, tip member 174 is configured with a 0.5 mm radius. As will be explained in further detail below, the configuration of tip member 174 is designed to gently displace and move the tissue into which it is inserted; i.e., atraumatically dilate the tissue to allow for introduction in to an intra-fascilar and para-fascilar manner, as opposed to cutting tissue as surgical access assembly 100 is inserted into the tissue.

Figure 9A:
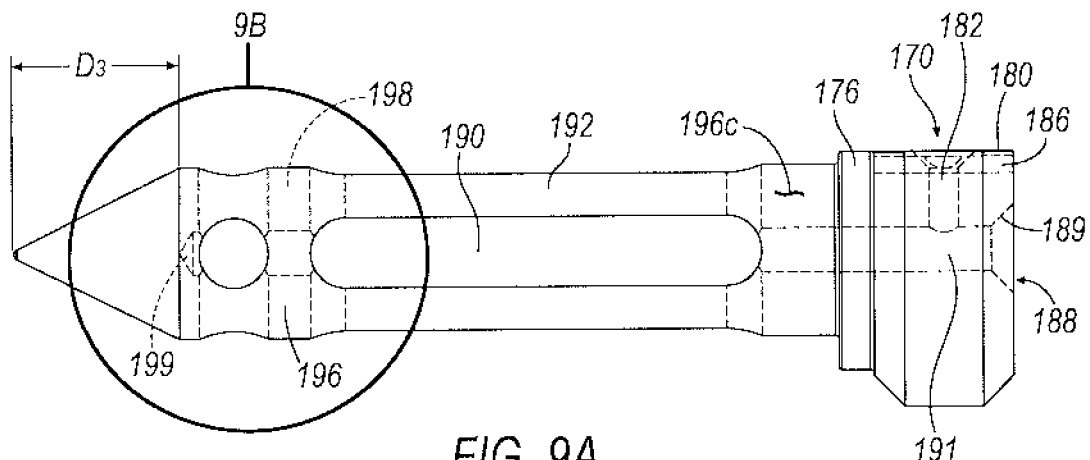
FIG. 9A is a side elevational view of the obturator assembly of FIG. 7A.

Handle portion 170 is positioned at proximal end 166 of obturator 104. As best seen in FIGS. 7B, 8A and 9A, handle portion 170 comprises a stop member 176 and a grip member 178. Stop member 176 is positioned distally of grip member 178 and, as best seen in FIG. 8A, is configured to have a width W1 that is greater than a diameter D1 of body portion 168, as well as a diameter D2 of outer sheath 102 (shown in FIG. 4A). Grip member 178 is configured with a width W2 that is greater than the width W1 of stop member 176, thereby providing a step-like configuration. Stop member 176 further defines an engagement surface 177 that is axially spaced from a distal surface 179 of grip member 178.

Figure 7A:
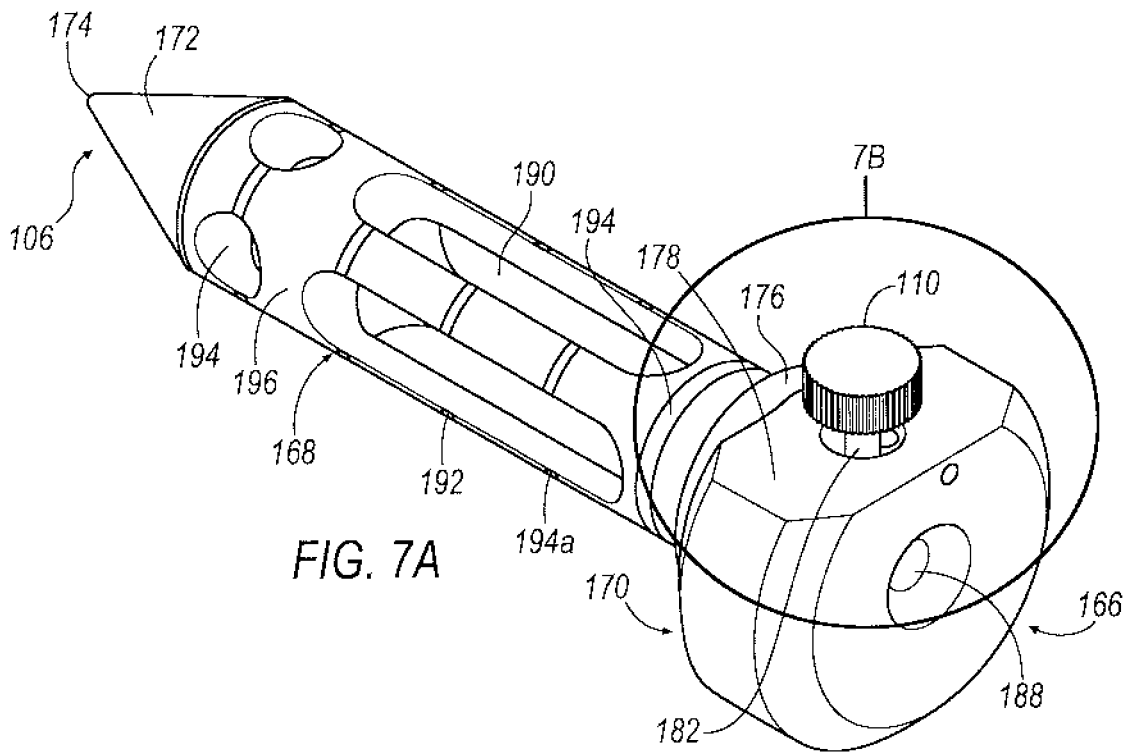
FIG. 7A is a perspective view of an obturator assembly of the surgical access assembly of FIG. 2.
Figure 7B:
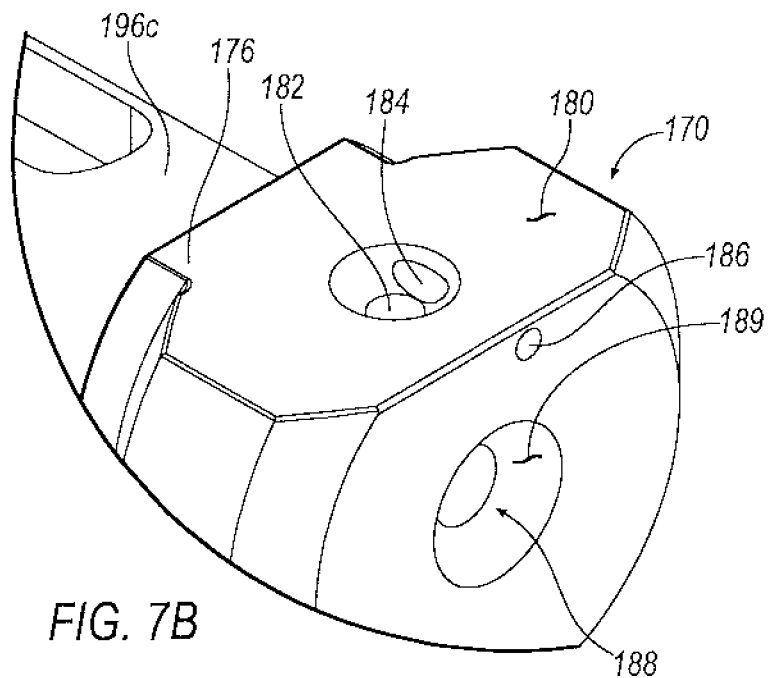
FIG. 7B is an enlarged view of an end face of the obturator assembly taken from area 7B of FIG. 7A.
Figure 10:
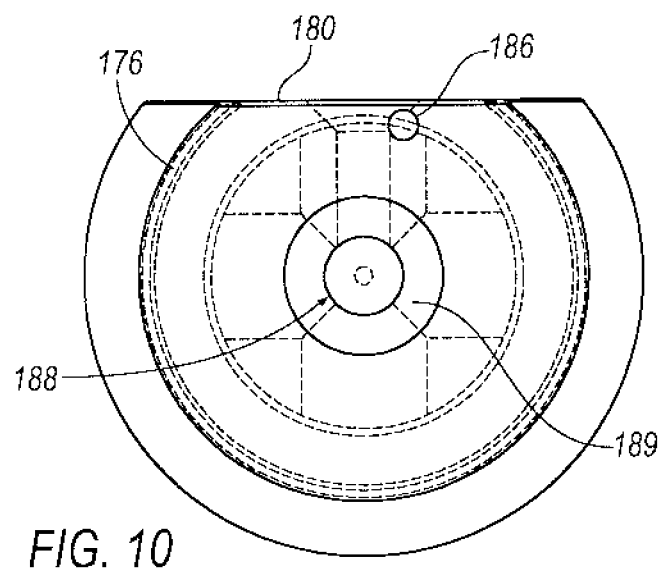
FIG. 10 is an end view of the obturator assembly of FIG. 7A.

In one exemplary arrangement, handle portion 170 is configured with a generally planar surface 180, as best seen in FIGS. 7A-7B and FIG. 10. Planar surface 180 is configured with a receiving aperture 182 that is configured to receive locking member 110. In one exemplary arrangement, receiving aperture 182 is threaded. As best seen in FIGS. 2, 7B, and 8A, disposed within receiving aperture 182 is an engagement opening 184. Engagement opening 184 is in communication with a channel 186 (seen in phantom in FIGS. 8A and 9A) that extends at least partially thorough handle portion 170. After locking member 110 is at least partially engaged within receiving aperture 182, retaining member 114 (FIG. 2) is positioned within channel 186. Because engagement opening 184 opens into receiving aperture 182, a portion of retaining member 114 extends across a portion of receiving aperture 182 such that locking member 110 is prevented from being entirely withdrawn from receiving aperture 182. For example, locking member 110 is illustrated as having threads that cooperate with corresponding internal threads in receiving aperture 182. Retaining member 114 is positioned within channel 186 so as to extend above the threads of locking member 110 such as locking member 110 is being removed from receiving aperture 182, threads come into contact retaining member 114, thereby preventing complete removal of locking member 110 from handle portion 170.

An access opening 188 is formed through proximal end 166. Access opening 188 extends through handle portion 170. In one exemplary arrangement, access opening 188 may be provided with an inwardly extending chamfer 189 that tapers toward access opening 188. Chamfer 189 provides a self-directing feature for inserting navigation member 112 into access opening 188. Access opening 188 is in communication with a first channel segment 191 that extends through handle portion 170 and into body portion 168.

Figure 8D:
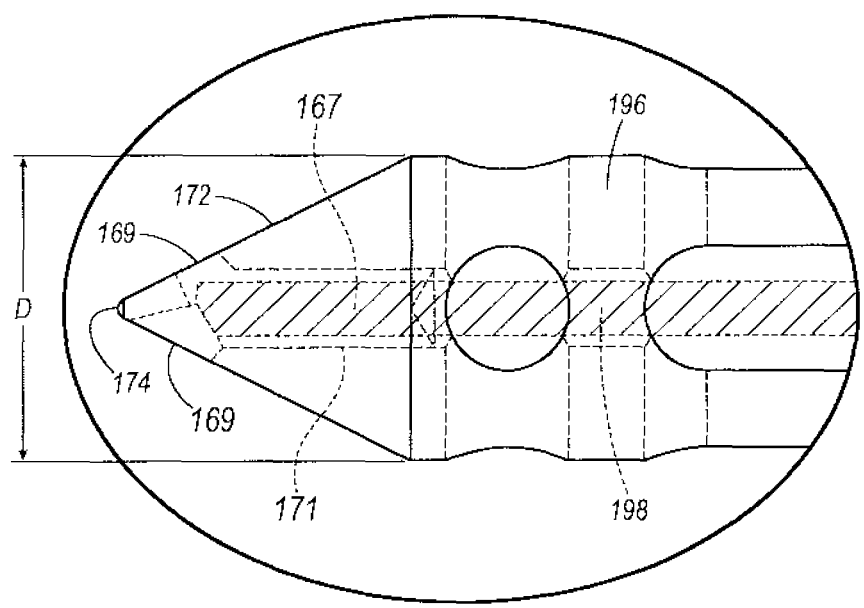
FIG. 8D is an alternative embodiment of the distal end of the obturator assembly taken from area 8B of FIG. 8A.

As seen in FIG. 8D, obturator 104 may further be configured to receive a viewing member 167 operatively connected thereto. More specifically, conical tip portion 172 may be configured with one or more viewing windows 169 that are oriented to be flush with the surface of conical tip portion 172. Viewing windows 169 are in communication with a viewing member channel 171 that may selectively receive a viewing member such as, for example, a fiber optic cable or an ultrasound probe. The viewing member may be in addition to the use of navigation member, or in place thereof. The viewing member permits the surgeon to observe, in real-time (i.e., during insertion), surrounding tissue and eloquent tissue structures so as to minimize trauma during insertion.

Body portion 168 extends between distal end 106 and proximal end 166. Body portion 168 includes one or more elongated void areas 190. Void areas 190 serve to reduce weight of obturator 104, thereby making obturator 104 easier to manipulate during surgical procedures. Void areas 190 also facilitate sterilization of obturator 104 by moisture retention within body portion 168 of obturator 104. Further, void areas 190 also provide venting, thereby preventing a vacuum from being generated as obturator 104 is being withdrawn from outer sheath 102 during operation.

Void areas 190 are separated by web portions 192 that extend axially through a portion of the length of body portion 168. Disposed on web portions 192 of body portion 168 are one or more indicators 194. Indicators 194 may include spaced apart hash marks (designated as 194A) that cooperate with an imaging modality to provide information, in real-time, concerning the location of obturator 104 relative to various tissue, critical structures, and fascicles within the brain, while obturator 104 is positioned within tissue. Indicators 194 also assist with providing information to regarding the relative positions between obturator 104 and outer sheath 102. Indicators 194 produce a signal void or minimal artifact under certain imaging modalities.

Body portion 168 may further include one or more cross webs 196. Cross webs 196 are oriented transverse to web portions 192 and connect web portions 192 together. In one exemplary arrangement, body portion 168 includes at least one cross web 196 that operatively defines the outer diameter D2 of body portion 168. Diameter D2 is sized to fit within lumen 148 of outer sheath 102 such that obturator 104 and outer sheath 102 may be selectively slid relative to one another. However, diameter D2 is also sized to minimize or even eliminate any gaps between an inner surface of outer sheath 102 and an outer surface of obturator 104. In the exemplary arrangement shown in FIG. 7-9, three cross webs 196A, 196B and 196C are provided. A first cross web 196A is connected to distal tip portion 172, while second cross web 196B is spaced proximally from first cross web 196A and separated by a void area 193. Third cross web 196C is separated from second cross web 196B by void areas 192 and is positioned distal from first stop member 176 of handle portion 170. Cross webs 196 serve to provide for structural integrity of obturator 104, as well as improved rigidity.

In one exemplary arrangement, one or more of cross webs 196 may further be provided with an annular compensating protuberance 197 to accommodate for slight manufacturing variations of the diameter of lumen 148 of outer sheath 102. For example, as it is contemplated that outer sheath 102 may be a component that is molded from a resin, a process which may produce such slight manufacturing variations. Compensating protuberance 197 extends slightly radially outwardly from an outer surface of obturator 104 and cooperates with lumen 148 of outer sheath 102 to create a friction fit between the outer surface of obturator 104 and lumen 148, due to the slight flexibility of the resin of outer sheath 102. Use of compensating protuberance 197 thereby reducing the need for maintaining a high dimensional tolerance of outer sheath 102 in production.

Figure 9B:
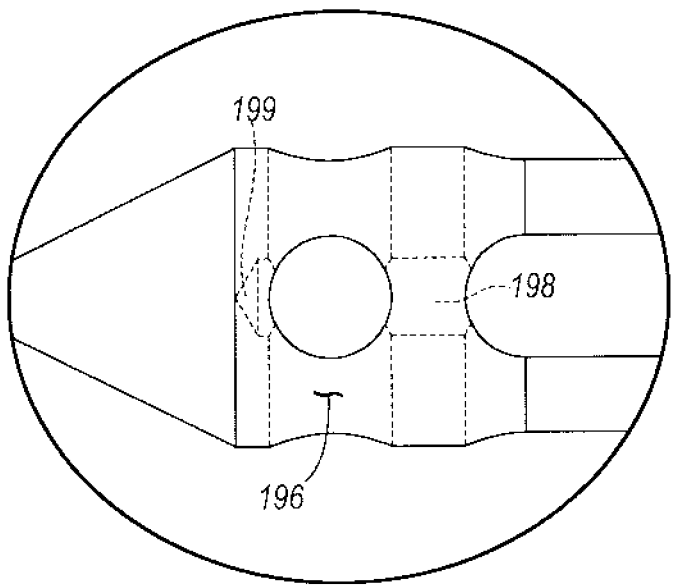
FIG. 9B is an enlarged view of a portion of the obturator assembly taken from area 9B of FIG. 9A.

In one embodiment, cross web 196B is provided with a second channel segment 198 (shown in phantom) that extends there through. Second channel segment 198 is axially aligned with first channel segment 191 and is configured to selectively receive navigation member 112. In one exemplary arrangement, disposed in first cross web 196A is an inwardly extending depression 199, as best seen in FIG. 9B. Depression 199 is configured in such a manner so as to align a distal tip of navigation member 112 with distal end 108 of outer sheath 102, when outer sheath 102 is assembled to obturator 104.

Referring to FIGS. 11A-11F, details of an optional illuminating ring 300 will now be described. Illuminating ring 300 is generally defined by a top surface portion 302, a wall member 304. A circuit board 306 may also be provided. Top surface 302 includes at least one access opening 308 therethrough that is configured to receive one or more surgical instruments, as will be described below in further detail. Additional small openings 309 may be provided in top surface 302. One or more of small openings 309 are configured to be aligned with small openings 150 disposed on flange member 142. Wall member 304 extends from top surface 302 so as to create an open cavity 310 within illuminating ring 300. An outer surface of wall member 304 may be textured (not shown), similar to grip ring 120.

One or more light elements 312 that are supported by a portion of illuminating ring 300. In one embodiment, shown in FIG. 11E, lights 312 are fixedly mounted to top surface 304 so as to face inwardly toward open cavity 310, adjacent access opening 308. Each light 312 is electrically connected to a remote power source (not shown) by wires 314. In one exemplary arrangement, wires 314 may be retained within channels formed in top surface 302 around access opening 308.

In an alternative arrangement (FIG. 11F), lights 312 may be incorporated in a circuit board 306. Circuit board 306 is configured with an access opening 316 that may be aligned with access opening 308 formed in top surface 302. Further, circuit board 306 is also sized to be positioned within open cavity 310, and fixed thereto. In other words, in one arrangement, circuit board 306 is sized to have an outer diameter that is smaller than an inner diameter defined by wall member 304. A wall opening 318 may be formed through a portion of either top surface 302 or wall member 304 to provide access for wires 320 to electrically connect circuit board 306 to a power source. An example of wall opening 318 may be seen in FIGS. 11B, 11D, and 11F. Circuit board 306 may be configured such that there is a constant output of light when illuminating ring 300 is turned on so that there is a steady state.

Figure 11G:
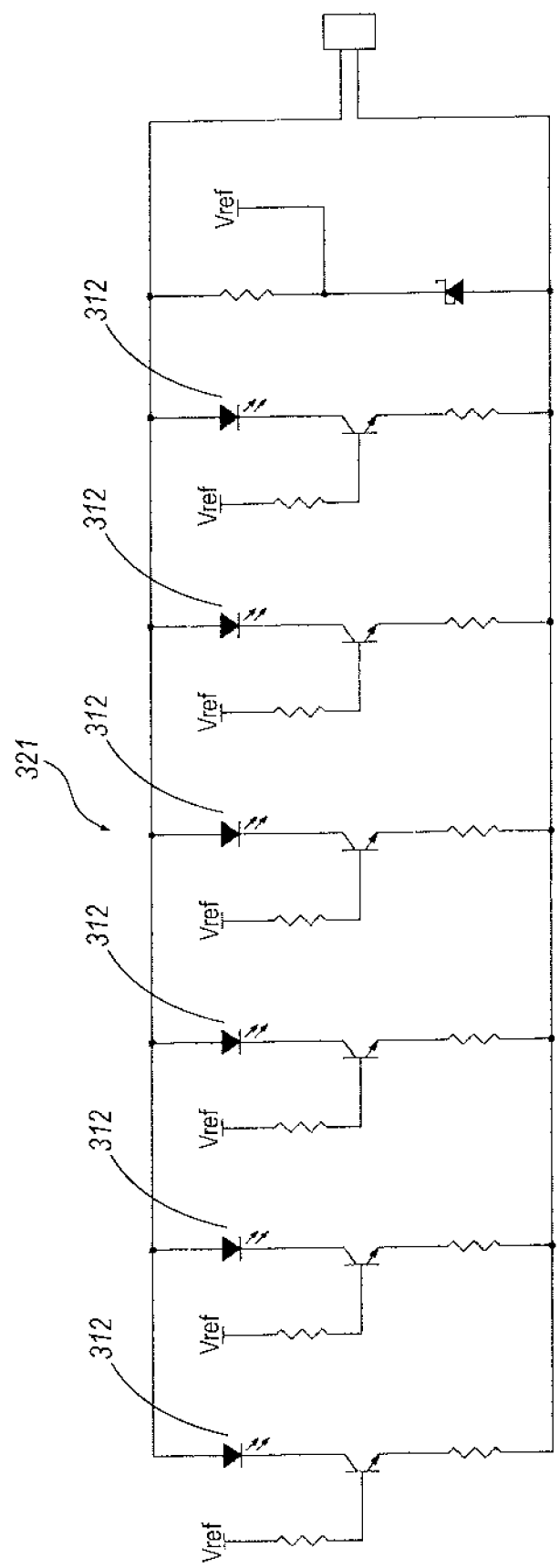
FIG. 11G is an exemplary electrical schematic for use with the illuminating ring of FIG. 11A.

An exemplary circuit design 321 is depicted in FIG. 11G for circuit board 306. In the exemplary configuration, circuit design 321 is configured to prevent flickering of lights 312 and/or prevent operation of less than all of the lights 312 during use of illuminating ring 300. More specifically, circuit design 321 is configured such that if one light 312 burns out, or if batteries that supply power to circuit get low, illuminating ring 300 will simply shut off and a replacement battery pack (not shown) may be used.

In one exemplary arrangement, lights 312 are LED lights, although other light devices may be utilized. LED lights do not contribute significantly to the weight of surgical access assembly 100, and also dissipates a non-clinical significant amount of heat. Moreover, LED lights can emit different combinations of colors/frequencies of light that may be incorporated to illuminating ring 300, to provide improved visualization of fluorescing dyes which allow for the differentiation of tissues.

Use of LED lights also allow for an endoscope to be used with surgical access assembly 100, but without an accompanying fiber-optic light source. This arrangement significantly reduces a required overall outside diameter of the endoscope, which improves the working space within lumen 148 of outer sheath 102. More specifically, lumen 148 of outer sheath 102 has more available working space, thereby providing increased simultaneous use of multiple instrumentation, as well as improved visualization. Further, because traditional endoscope devices must be attached to a supporting structure that is fixed to an introducer cannula, the weight of such an assembly tends to pull on the introducer cannula, in one direction. This action can compromise the placement of the introducer cannula during the procedure and/or cause trauma to brain tissue. Thus, by incorporating illuminating ring 300 to outer sheath, such potential disadvantages may be avoided.

While illuminating ring 300 may be secured to grip ring 120 of outer sheath 102 in any suitable manner, in one exemplary arrangement, illuminating ring 300 is provided with a selective locking arrangement to selectively fix illuminating ring 300 to grip ring 120. In one exemplary arrangement, wall member 304 is provided with a locking channel 322, best seen in FIG. 11B. Locking channel 322 comprises wall opening 318 and that opens into a first channel segment 324, and a second channel segment 326 that is in communication with first channel segment 324. Wall opening 318 extends from a bottom surface 328 of wall member 304. Second channel segment 326 is spaced upwardly from bottom surface 328 of wall member 304 and is oriented at an angle from first channel segment 324. In one exemplary arrangement, second channel segment 326 is oriented 90° from first channel segment 324.

Figure 12:
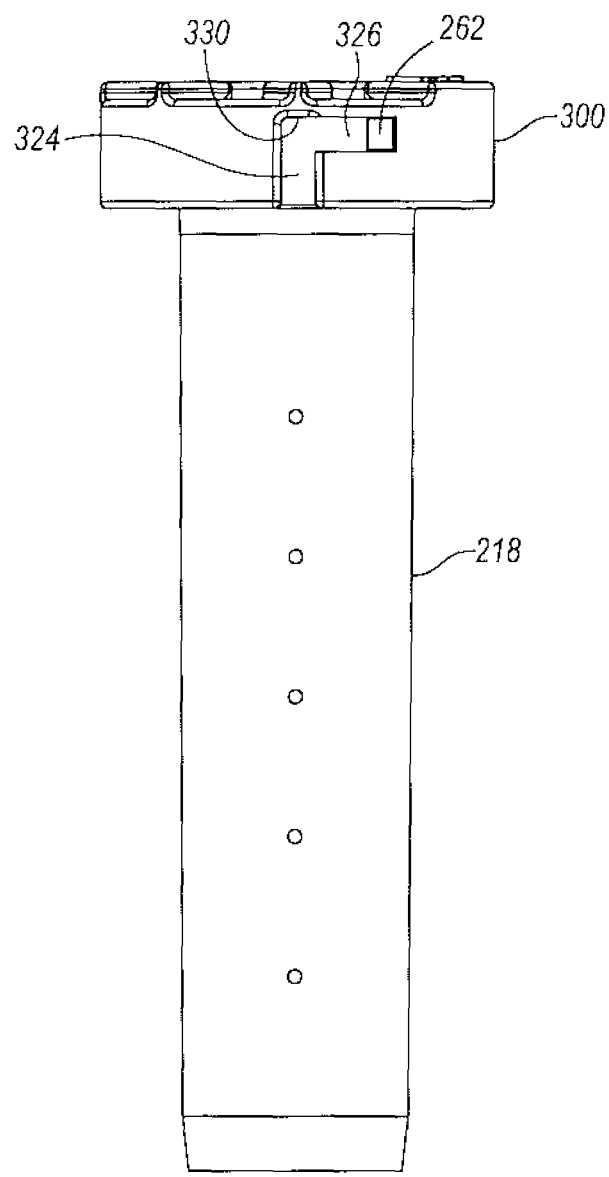
FIG. 12 illustrates the illuminating ring of FIG. 11A assembled to an exemplary embodiment of the outer sheath.

Locking channel 322 cooperates with locating member 262 to selectively secure illuminating ring 300 to grip ring 120. More specifically, illuminating ring 300 is pushed down over grip ring 120 with locating member 262 entering wall opening 318. As illuminating ring 300 is pushed downwardly, locating member 262 travels through first channel segment 324. Once locating member 262 contacts a terminal end 330 of first channel segment 324, illuminating ring 300 is rotated relative to outer sheath 102 such that locating member 262 moves into second channel segment 326, thereby selectively locking illuminating ring 300 to outer sheath 102, as shown in FIG. 12. Once connected, illuminating ring 300 thereby provides a hands-free light source to illuminate lumen 148 of outer sheath 102.

In one exemplary arrangement, certain segments of outer sheath 102 may be frosted so as to reflect light to increase visualization within outer sheath 102. For example, tapered portion 130 may be frosted. Similarly, the top of grip ring 120 may also be frosted.

Figure 11H:
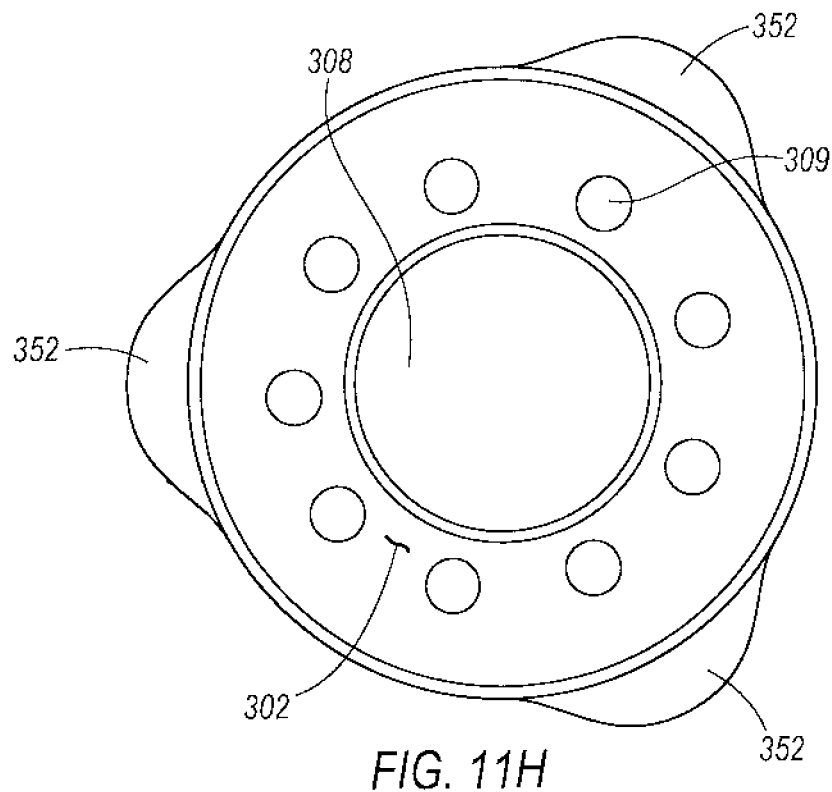
FIG. 11H is a top plan view of an alternative arrangement of the illuminating ring of FIG. 11A.
Figure 11I:
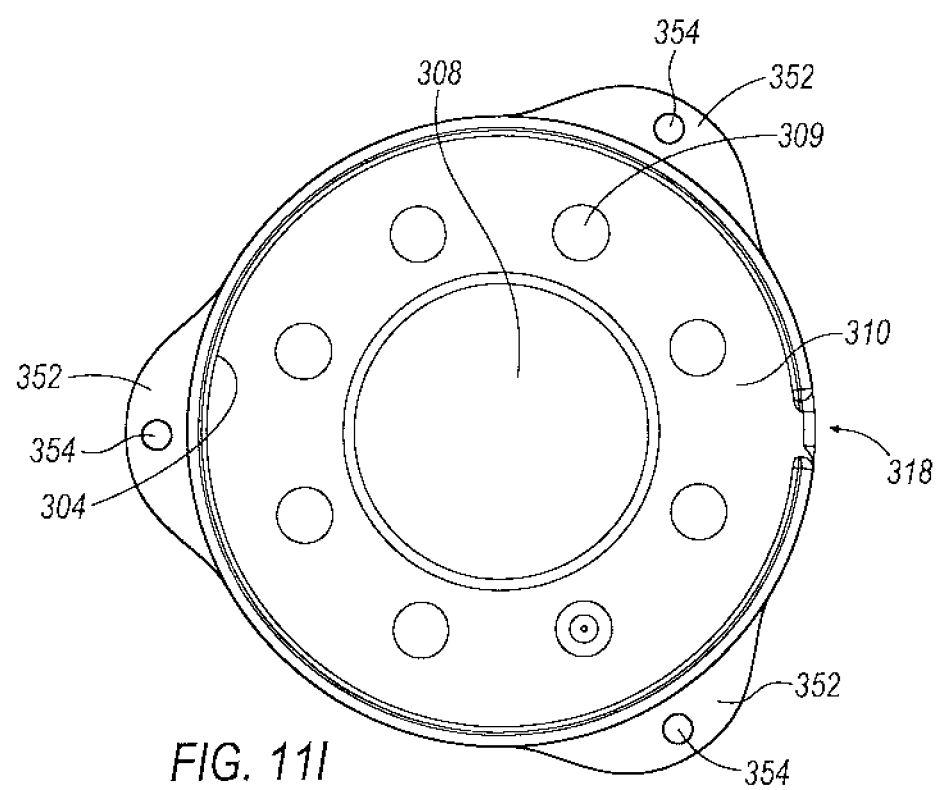
FIG. 11I is a bottom plan view of the illuminating ring of FIG. 11H.

Referring to FIGS. 11H-I, an alternative arrangement of illuminating ring 350 is shown. Illuminating ring 350 is similar to illuminating ring 300 and common elements, such as top surface 302, wall member 304, access opening 308, open cavity 310, small openings 309, and wall opening 318, are also shown in FIGS. 11H-I. The embodiment shown in FIGS. 11H-I further includes outwardly extending flange members 352. In one arrangement, flange members 352 are integrally formed with the outer periphery of illuminating ring 350. While the depicted embodiment includes three flange members 352 spaced equi-distantly about a periphery of a wall member of illuminating ring 300, it is understood that any number of flange members 352 may be provided. Further, flange members 352 may be arranged about the periphery in any arrangement.

Flange members 352 support sensors 354 (see FIG. 11I) or reflective balls that serve as position indicators. More specifically, sensors 354 are configurable to cooperate with a navigation system (to be explained in further detail below), to indicate the location of outer sheath 102 after insertion into an area of interest, once illuminating ring 300 is connected to outer sheath 102. In one arrangement, sensors 354 may be molded into or bonded onto flange members 352. In another arrangement, sensors 354 may be temporarily attached to flange members 352. For example, flange members 352 may each include a groove into which a sensor may be positioned, and a retaining ring may be secured over each sensor 354 to temporarily secure sensor to flange member 352.

In another exemplary arrangement, sensor 354 may be powered through circuit board 306. More specifically, sensors 354 may be electrically connected to circuit board 306. Additional wires electrically connect circuit board 306 to a power source to provide power not only to lights carried by illuminating ring 350, but also to sensors 354.

Operation of surgical access assembly will be described in connection with a process flow 400 illustrated in FIG. 13. However, as an initial note, while use of surgical access assembly 100 is initially described in connection with a tissue resection operation, it is understood that surgical access assembly 100 may simply be used to provide access to an area of interest within the brain to permit a user to interrogate the area of interest to learn about any abnormalities and/or diseases for evaluation and development of a treatment protocol, and/or to apply a therapy or treatment to deep seated locations within the brain.

Generally speaking, before any procedure is decided upon, a patient will first present with symptoms or deficits requiring evaluation. Thus, the start of process flow 400 begins with a surgeon making a determination 402 of the cause of such symptoms/deficits/abnormalities. In some instances, causes for such symptoms/deficits/abnormalities may be visibly apparent such that a determination may be made through use of a variety of imaging modalities, including, but not limited to, MRI or CT imaging. The process then proceeds to step 404.

If the determination from step 402 finds that a brain condition is found, such as a tumor, hematoma, or other abnormality, an additional determination is required. More specifically, a location of the brain condition is determined in step 404. If the imaging determines that an area of interest is located in the intra-axial/subcortical space, the process flow continues to step 406. However, if a brain condition is located in other, more easily accessible areas of the brain, the process flow stops.

Figure 14A:
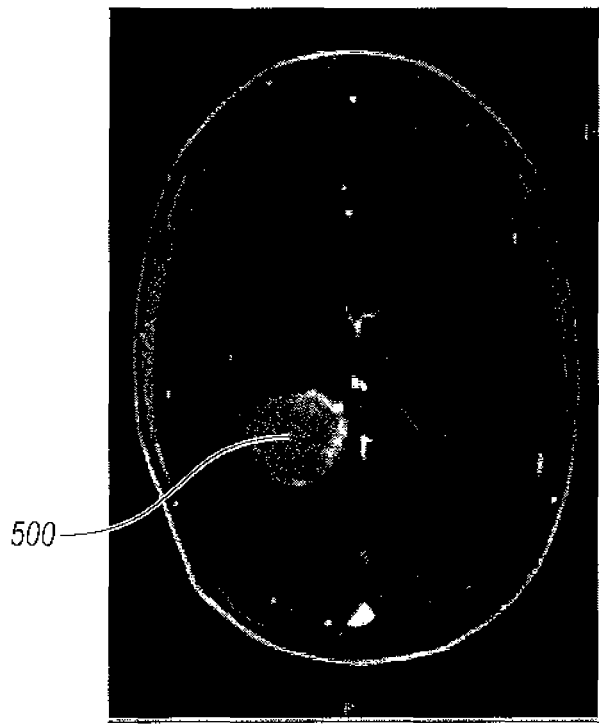
FIG. 14A-14B are images of a brain illustrating an area of interest, taken using an imaging modality.
Figure 14B:

As discussed above, any suitable imaging modality may be utilized to determine if a brain condition exists, and if so, where that brain condition is located. FIGS. 14A and 14B illustrate examples of imaging results from an MRI. More specifically, an area of interest 500, in this case a tumor, may be seen deep in the subcoritcal space.

Once area of interest 500 is located, at step 406 an additional imaging sequence is employed to determine the location of eloquent structures such as vessels and fiber tracts and the associated fascicles so as to plan the safest access route to the area of interest. Exemplary arrangements for accomplishing this step include CT-Angiography and MRI with Diffusion Tensor Imaging (DTI) sequences. DTI allows for the determination of directionality as well as the magnitude of water diffusion along the communication "wiring" pathways called fiber tracts and fascicles. This kind of MRI imaging can provide imaging to allow for the estimation of potential damage to nerve fibers that connect the areas of the brain which can be affected by a stroke, for example, to brain regions that are distant from it, and can also be used to visualize white matter fibers in the brain and can map (trace image) subtle changes in the white matter associated with functional diseases such as multiple sclerosis and epilepsy, as well as assessing diseases where the brain's wiring is abnormal, such as schizophrenia, as well as tumor involvement.

Diffusion Tensor Tractography (DTT) may also be used. DTT allows for noninvasive tracking of neuronal fiber projections in a living human brain. White matter fiber trajectories are reconstructed throughout the brain by tracking the direction of fastest diffusion, which is assumed to correspond to the longitudinal axis of the tract. Diffusion tensor tractography provides insight into white matter integrity, fiber connectivity, surgical planning, and patients' prognosis. Once the imaging information has been analyzed, the process then proceeds to step 408.

Figure 15:
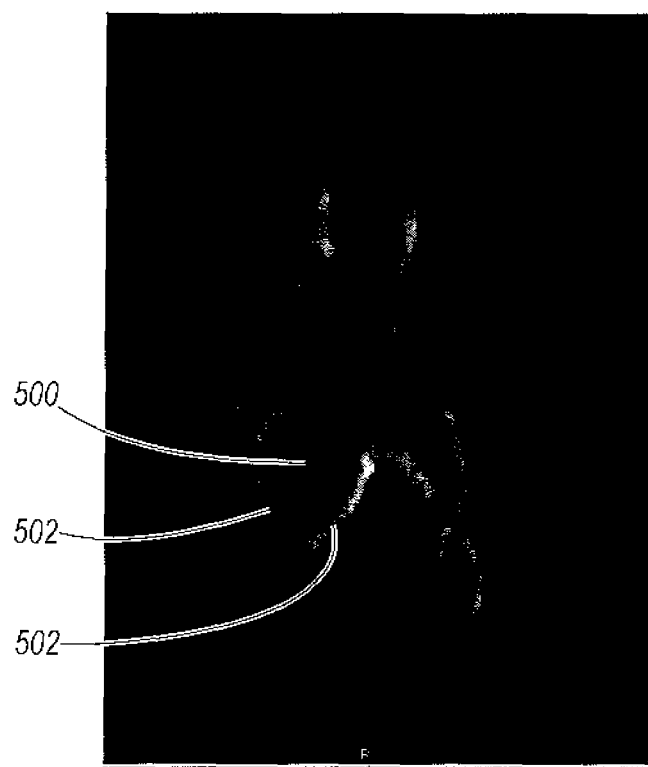
FIG. 15 is an image taken of the brain shown in FIGS. 14A-14B, illustrating various critical structures, such as fiber tracts and fascicles of the brain.

Referring to FIG. 15, an example of DTI imaging of the brain shown in FIGS. 14A and 14B is depicted. A map of fascicles and other vessels are illustrated in FIG. 15, including major vessels 502 that are shown spread around area of interest 500. Such images provide the surgeon with valuable information about potential avenues for access tracts to area of interest 500.

In step 408, a plan for the operative trajectory is developed. More specifically, imaging information is used to plan (either manually or with software) the access tract/pathway to achieve fiber tract involvement during access to the area of interest. In evaluating fiber tract involvement from a potential access tract/pathway, consideration of fiber tract importance may be based on an individual patient's occupational and personal needs and/or preference. Once a pathway has been planned, the process proceeds to step 410.

In step 410, image data from the MRI/DTI and CT/CTA image sequence obtained during step 406 is input into an intraoperative navigation system. Intraoperative navigation systems may be used to provide direct visualization of area of interest 500 in real time, as surgical access system 100 is being positioned within the brain. The method then proceeds to step 412.

Once the procedure has been planned and the image data has been uploaded to a navigational system, step 412 requires that the appropriate sized surgical access assembly 100 is selected. First the appropriate size of a craniotomy must be determined. Further, the present disclosure contemplates that different diameter and length sizes of surgical access assembly 100 may be employed, the size depending on the particular location of area of interest 500. Accordingly, step 412 requires that the surgeon select the appropriate length and diameter of surgical access system 100 to be used, based on the physical and location characteristics of the area of interest 500. Once surgical access assembly 100 is selected, the process proceeds to step 414.

In step 414, the surgeon creates the craniotomy and Dural access incision. The process then proceeds to step 416.

In step 416, the obturator 104 is inserted into outer sheath 102 until grip ring 120 abuts first stop member 176, as shown in, for example FIG. 2. Navigation member 112 is then operatively connected to obturator 104.

As discussed above, various types of navigation members 112 may be employed with surgical access assembly 100. In one exemplary configuration, navigation member 112 is configured as a probe (as shown in FIG. 2). In this configuration, navigation member 112 is inserted through access opening 188 of grip member 178 until a distal tip 417 of navigation member 112 is deposited into depression 199 (see FIG. 9B). Depression 199 is formed so that distal tip 471 of navigation member 112 is positioned within the same plane as distal tip 132 of outer sheath 102, when obturator 102 and outer sheath 104 are assembled together as shown in FIG. 2. Locking member 110 may be tightened to fixedly retain navigation member 112 within obturator 102. A portion of navigation member 112 will extend proximally from grip member 178 and will be operatively connected to a navigation system that includes a screen that visually illustrates the information obtained from the imaging sequences, along with the trajectory of surgical access system 100. Thus, with the navigation member 112 operatively connected to a navigation system, the position of distal tip 132 of outer sheath may be indicated, in real time, while surgical access system 100 is being navigated within a body.

In another configuration, the software operating the navigation system may further be provided with an offset dimension that corresponds to a distance D3 between distal tip 174 of obturator 104 and distal tip 132 of outer sheath. In this arrangement, a dotted line may appear on the navigation screen that indicates where distal tip 174 of obturator 104 is located, in real-time.

Navigation member 112 may further be provided with image guidance position indicators, such as an array of reflectors of the type use in connection with optical image guidance systems. The infrared reflectors used with such a system are mounted to a handle of a probe-like navigation member 112 in a customary triangular configuration calibrated to identify the tool to the image guidance system. Such imaging systems are available, for example Medtronic Surgical Navigation Technologies (Denver, Colo.), Stryker (Kalamazoo, Mich.), and Radionics (Burlington Mass.).

Typically, the positioning of the indicators is calibrated such that the image guidance system can project an image of the tool onto a display of images of the patient's brain, such as MRI images used to plan surgery. Thus, as discussed above, as surgical access system 100 is inserted, the surgeon can see the relative position of system 100 relative to the structures of the brain as reflected on images, and particularly with respect to the target tissue.

Other guidance systems, such as magnetic or electromagnetic or radio transmitting systems may also be used, and the illustration of infrared reflectors and discussion of optical image guidance systems are exemplary only and are not intended to be limiting. In addition, while the exemplary method has been described in connection with superimposing an image of surgical access system 100 onto a pre-operative image, it is contemplated that real-time imaging capability may be utilized and that the image of surgical access system 100 may then be shown in relation to the surrounding tissue structures on a real time image.

In another exemplary configuration, an RFID chip may be embedded in obturator 104 that operatively communicates information to a navigation system or other surgical system about the specific attributes, such as, but not limited to, length and diameter. This information may be used to facilitate placement with the navigation system or other systems for information display or trajectory and location calculations during placement of obturator 104.

Figure 16A:
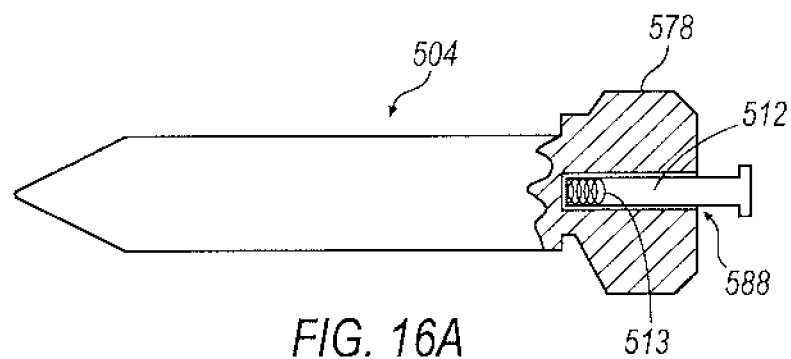
FIG. 16A is an alternative embodiment of an obturator with an imaging device operatively connected thereto.
Figure 16B:
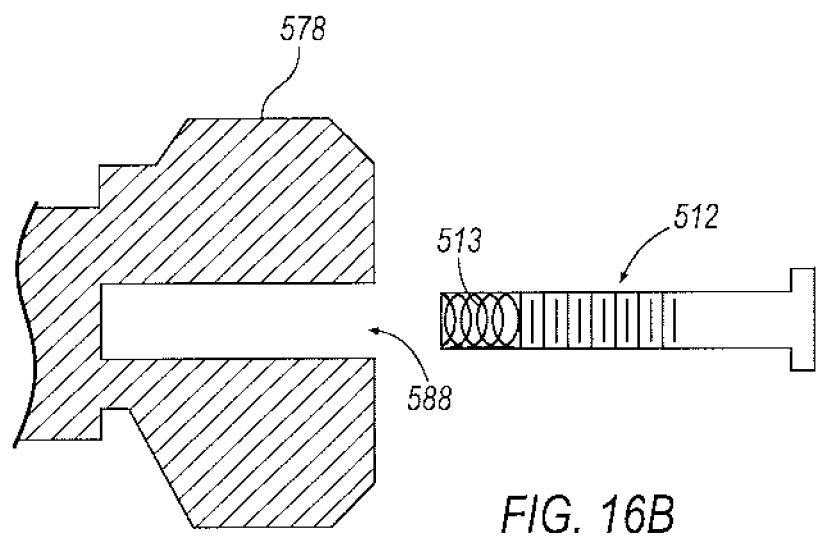
FIG. 16B is a partially exploded view of an enlarged cross-sectional view of the proximal end of the obturator and post.

In yet another exemplary arrangement, as shown in FIGS. 16A-16B, an alternative embodiment of an obturator 504 may be used, wherein the obturator 504 is configured with a post 512 that is configured to operatively attach a navigation array. Post 512 may be detachably or permanently connected to grip member 578 of obturator 104. For example, as shown in FIG. 16A, post 512 is configured to be selectively detachable and may be used to capture a small coil 513 for Mill tracking of surgical access assembly 100. A portion of post 512 may be threaded and an access opening 588 formed in a proximal face of grip member 578 have be provided with corresponding threads (not shown) so as to affix post 512 to obturator 504. Other manners of selectively affixing post 512 to obturator 504 are also contemplated, including, but not limited to, a locking member 110 arrangement similar that shown in FIG. 2. As also discussed, post 512 need not be selectively detachable. Indeed, it is contemplated that post 512 may be permanently affixed to obturator 504, in any suitable manner, whereby the navigation array may be secured to post 512. In yet another alternative arrangement, obturator 504 may be configured such that a post, which is an element of the array itself, may be attached.

Figure 16C:
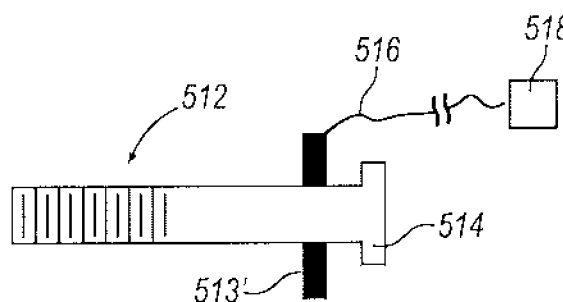
FIG. 16C is an alternative arrangement of a coil sensor for use with an obturator.
Figure 16D:
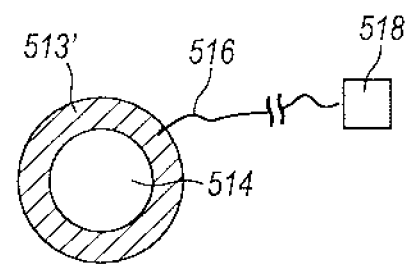
FIG. 16D is an end view of the coil sensor mounted on the post of FIG. 16C.

In still a further alternative arrangement, referring to FIGS. 16C-16D, a coil sensor 513' may be configured to be disposed about an outer periphery of post 512. In this arrangement, coil sensor 513' is slid or otherwise mounted to post 512 such that when post 512 is operatively attached to obturator 504 coil sensor 513' is captured between a portion of grip member 578 and a proximal end portion 514. A connecting wire 516 operatively attaches coil sensor 513' to an image position console 518.

Once surgical access assembly 100 is assembled and operatively connected to a navigational system, the process then proceeds to step 418, in which surgical access assembly 100 is navigated to area of interest 500. In one exemplary arrangement, distal tip 178 of obturator 104 is directed to a furthermost outer margin of area of interest 500. In other arrangements, distal tip 178 is positioned directly at the area of interest 500. Referring to the arrangement in FIG. 14B, for example, surgical access assembly 100 is directed along a trajectory T that extends through area of interest 500 to a location 501 that may be positioned within the margins of area of interest 500 or even slightly beyond the margin. In other words, surgical access system may be directed to be positioned at or adjacent an area of interest 500.

Due to the tapered configuration and closed, radiused distal tip 174 of obturator 104, as well as the radiused distal tip 132 of outer sheath 102, as surgical access assembly 100 is inserted into the brain and navigated to area of interest 500, tissue is gently pushed to either side of surgical access assembly 100, so as to atraumatically dilate tissue, while minimizing trauma to the tissue. Further, because surgical access assembly 100 is operatively connected to navigation member 112, as surgical access assembly 100 is being inserted into the brain tissue, navigation member 112 may cooperate with an imaging modality to providing real-time information concerning fiber tact in trajectory T, thereby allowing the surgeon to minimize fiber tract compromise or damage during insertion of surgical access assembly 100. Once surgical access assembly 100 is positioned at area of interest 500, the process proceeds to step 420.

As step 420, navigation member 112 removed from or detached from surgical access assembly 100. The process then proceeds to step 422.

Figure 17A:
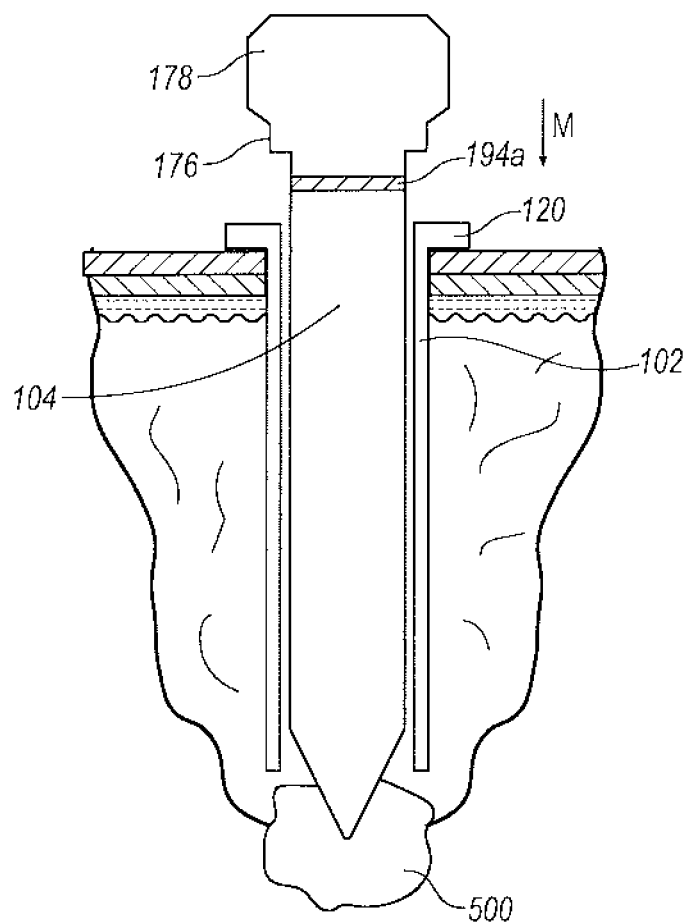
FIG. 17A is an elevational view of the surgical access system, while the obturator is being withdrawn from the outer sheath.

Once navigation member 112 is removed, outer sheath 102 is then operatively positioned with respect to area of interest 500. More specifically, as shown in FIG. 17A, outer sheath 102 is decanted with respect to obturator 104 such that distal end 108 of outer sheath 102 is moved toward distal end 106 of obturator 104, as indicated by arrow M. This action is accomplished by grasping grip ring 120 with one hand while maintaining obturator 104 stationary, such, for example, grasping grip member 178 with another hand. Grip ring 120 may be gently rotated and/or swiveled with respect to a central axis of obturator 104 to enable outer sheath 102 to be moved distally with respect to obturator 104. First stop member 176 aids in gripping and manipulating outer sheath 102, in that a gap 423 (see FIG. 2) is created between end surface 158 and a distal end surface of grip member 178. Outer sheath 102 is decanted until grip ring 120 aligns with indicator 194A (see FIG. 7A). Indicator 194A is spaced from first stop member 176 a distance that generally corresponds to the length of distal tip portion 172 of obturator 104. Accordingly, when grip ring 120 is aligned with indicator 194A, distal end 108 of outer sheath 102 is aligned tip member 174 of obturator 104. Moreover, outer sheath 102 is positioned within area of interest 500. The process then proceeds to step 424.

Figure 17B:
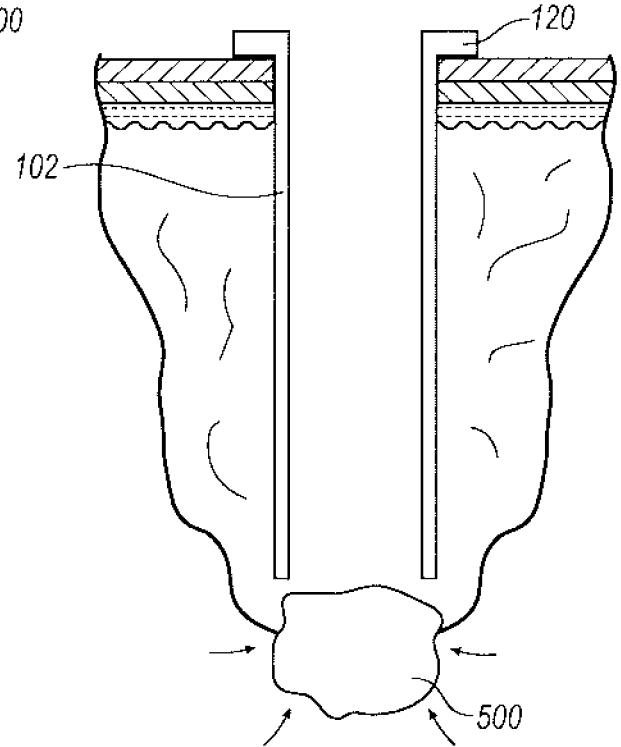
FIG. 17B is an elevational view of the surgical access system with the outer sheath in place within the brain.

In step 424, once outer sheath 102 is appropriately positioned, obturator 104 is then removed from outer sheath 102, as shown in FIG. 17B. More specifically, outer sheath 102 is maintained to be relatively stationary at area of interest 500, and obturator 104 is moved in a proximal direction until fully removed from outer sheath 102. This action results in outer sheath 102 forming a pathway to area of interest 500; a pathway that not only circumvents the need to cross the blood brain barrier for the delivery of therapy, but also provides direct access to the area of interest within the patient, thereby allowing previously inaccessible brain tissue to be accessed and interrogated, as well as permitting therapy to be applied, as will be explained in further detail below.

In other embodiments, rather than provide obturator 104 with navigation member 112, or in addition to providing obturator 104 with navigation member 112, as discussed above, outer sheath 102 may be provided with and RFID chip or sensor. With this configuration, the RFID chip or sensor of outer sheath 102 cooperates with the navigation system thereby making outer sheath 102 visible to the user on the navigation system, independent of obturator 104. Thus, once obturator 104 is removed from outer sheath 102, the location within the patient of outer sheath 102 will still be visible to the navigation system.

More specifically, the navigation system works with the additional images taken during the imaging sequence in step 406. The images taken in step 406 are uploaded into the intraoperative navigation system, as indicated in step 410. The RFID chip and/or sensors are configured to be read by the navigation system and place an image of outer cannula 102, thereby allowing the surgeon to direct visualize the location of outer cannula 102, while positioned within the patient.

Once outer cannula 102 is positioned at the area of interest 500 and obturator 104 is removed, one of the illuminating rings 300, 350 may be attached to outer sheath 102.

In one exemplary arrangement, rather than employing an RFID chip and/or sensor in outer sheath 102, illuminating ring 350 may be provided with sensors or reflective balls, as described above in connection with FIGS. 11H-I. With this type of configuration, once obturator 104 and outer sheath 102 have been delivered to area of interest 500 and obturator 104 is removed from outer sheath 102, illuminating ring 350 is operatively connected to outer sheath 102. Because illuminating ring 350 includes a navigational element, such as sensors and/or reflective balls, once illuminating ring 350 is connected to outer sheath 102, the navigation system will be able to "read" where outer sheath 102 is located in the body. In other words, an image of outer sheath 102 will be able to be projected onto the static images uploaded into the navigational system.

Once outer sheath 102 is placed in its desired location, the process then proceeds to step 426.

In step 426, outer sheath 102 is then secured in place so as to prevent cranial pressure or general manipulation of instruments passing in and out of the sheath 102 from pushing or dislocating outer sheath 102 out of the brain tissue. In one exemplary arrangement, a securing member may be utilized with small openings 150 on grip ring 120 to temporarily secure outer sheath 102. For instances where illuminating ring 300 is used with surgical access assembly 100, small openings 309 in illuminating ring 300 align with small openings 150 of grip ring. Accordingly, securing members may also be utilized with small openings 309. However, the securing member may be secured so as to permit a limited degree of movement, as will be discussed below, so as to result in a floating system that permits selective repositioning. Suitable securing members include, but are not limited to, bridle sutures, flexible bands with retaining hooks, or even repositionable retractor arms. Additional alternative securing arrangements are disclosed below. Once outer sheath 102 is secured, the process then proceeds to step 428.

In some procedures where it is desired to remove tissue from the brain, the process proceeds to step 428, whereby debulking area of interest 500 may be conducted. Traditionally, a patient is given medication, such as, for example, Mannitol, before an intracranial operation to reduce intracranial pressure (ICP) of the brain prior to the surgery. Indeed, ICP is often experienced by patients due to the natural response of the craniotiomy and/or the present of an abnormality within the brain. The present inventors have found that it may be advantageous to omit or minimize the use of medication for reducing ICP. More specifically, by not reducing ICP, because the brain tends to occupy the available space within the skull, after obturator 104 is removed from outer sheath 102, the target tissue may have a tendency to flow into, and present itself into the open distal end 108 of outer sheath 102, due to the cranial pressure. Area of interest 500 may actually move into outer sheath 102 on its own, thereby assisting in the delivery and minimizing manipulation required of outer sheath 102 during the process.

It is contemplated that a wide range of surgical devices may be inserted into outer sheath 102 to remove tissue abnormalities. In one exemplary arrangement, it is contemplated that outer sheath 102 may have an inner diameter up to approximately 20 mm, to allow multiple instruments, such as graspers, dissectors, scissors, cautery and suction instruments to be inserted through outer sheath 102 to perform surgery.

Figure 18:
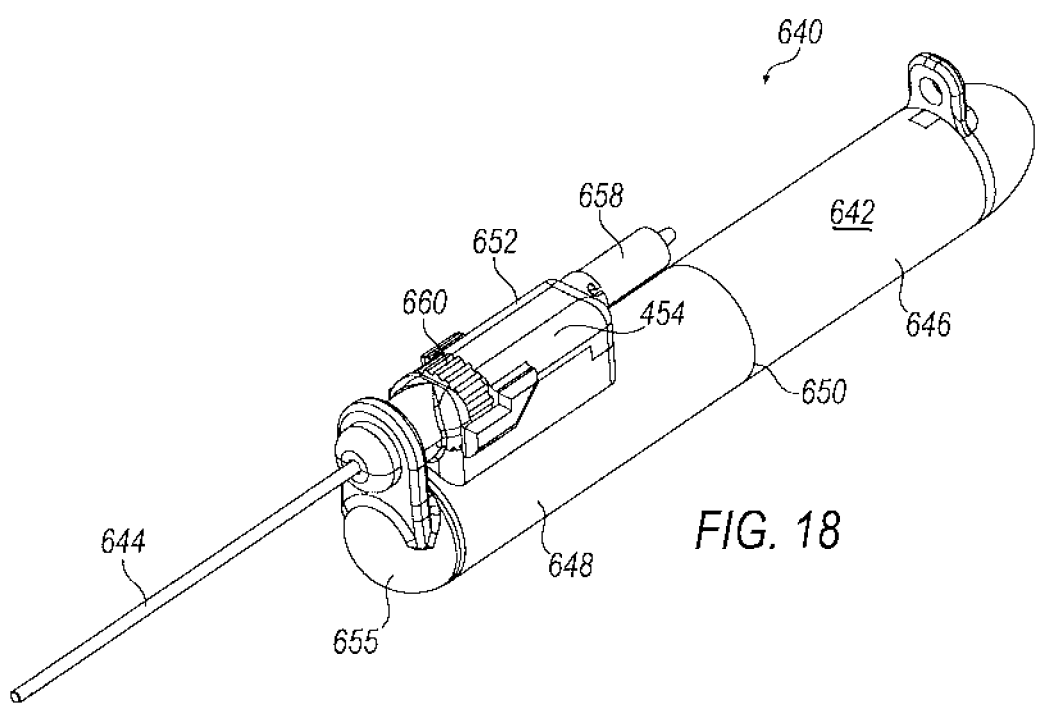
FIG. 18 is a perspective view of an exemplary surgical device used for cytoreduction.

One exemplary surgical device that may be used is the NICO MYRIAD® manufactured and distributed by Nico Corporation of Indianapolis, Indiana Referring to FIG. 18, an exemplary surgical cutting device 640 is shown, such as that disclosed in co-pending, and co-owned with the assignee of the present application, U.S. patent application Ser. No. 12/389,447, the contents of which are incorporated by reference in its entirety. Surgical cutting device 640 includes a handpiece 642 and a cutting element that includes an outer cannula 644 and an inner cannula (not shown). In one exemplary configuration, handpiece 642 is configured with a generally cylindrical shape. Handpiece 642 may be sized and shaped to be grasped with a single hand. Handpiece 642 also includes a lower housing 650 comprising a proximal section 646 and a distal section 648. A front housing section 655 may be connected to a cam housing positioned in distal section 648. An upper housing 652 is also provided. The cutting element is mounted to upper housing 652 and may be fluidly connected to a tissue collector 658. In one exemplary arrangement, tissue collector 658 may be operatively connected directly to upper housing 652. Alternatively, tissue collector 658 may be remotely connected to the cutting element by appropriate tubing. A vacuum line (not shown) may be connected to a proximal end of tissue collector 658 to direct tissue into the cutting element, as well as to deliver severed tissue to tissue collector 658. A rotation dial 660 for selectively rotating the outer cannula 644 with respect to handpiece 642 is also mounted to upper housing 652, to provide controlled cutting action.

Use of surgical device 640 is advantageous in that space is limited to effectuate tissue debulking, such that use of traditional surgical scissors may be challenging, especially when other instruments are inserted into outer sheath 102 simultaneously. Moreover, fibrosity of a tumor may present challenges for the use traditional suction debulking devices. Traditional graspers operate by tearing tissue of interest. However, the tearing action may become problematic if vessels or fascicles are too close to the tissue being torn in that such vessels or fascicles may also be torn.

Figure 19A:
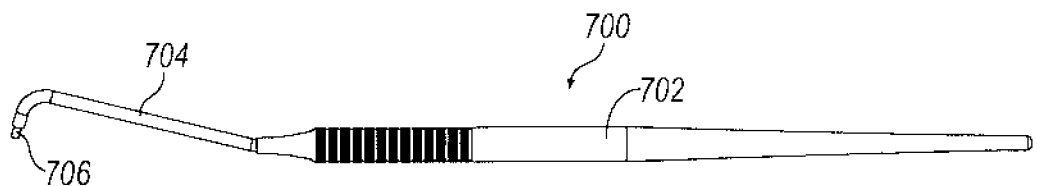
FIG. 19A is an elevational view of an exemplary manipulation member.
Figure 19B:
FIG. 19B is an elevational view of an alternative manipulation member.

In step 428, as area of interest 500 is cytoreductively debulked, it may become necessary to reposition or move outer sheath 102. If repositioning is necessary, the process moves to step 432. To that end, in one exemplary arrangement, manipulation members may be provided. Examples of manipulation members 700 and 700' are illustrated in FIGS. 19A-19B. Manipulation member 700 comprises a handle member 702 that supports an armature 704, and a hook element 706 that extends from armature 704. Hook element 706 is sized to fit within small openings 150 and 309 disposed within grip ring 120 and illuminating ring 300, respectively. In operation, hook element 706 is engaged with a small opening 150/309 and handle member 702 is used to gently push or pull outer sheath 102. Because outer sheath 102 is only loosely secured, outer sheath 102 may be selectively moved slightly for improved visualization or to access tissue. After outer sheath 102 has been repositioned, or if repositioning of outer sheath 102 is not necessary, the process moves to step 434, and cytoreduction of area of interest 500 continues.

In an alternative arrangement, manipulation member 700' may be secured to a flexible holder member 710. Manipulation member 700' comprises an armature 712 that carries a hook element 714 and an engagement portion 716. Engagement portion 716 operatively engages holder member 710 so as to fixedly secure manipulation member 700' to holder member 710, thereby freeing a surgeon's hand, once outer sheath 102 is positioned. It is understood that multiple manipulation members 700/700' may be utilized to permit a surgeon to selectively push or pull outer sheath 102.

Referring to FIGS. 19C-19F, other alternative arrangements for holding outer sheath 102 during a procedure are shown. More specifically, FIGS. 19C-19D illustrate a holding arrangement 720 that may be used with a Greenberg retractor assembly. Holding arrangement 720 comprises body portion 722, an engagement barrel 724, and a retaining member 726.

Body portion 722 may be configured as a relatively thin shaft. In one exemplary arrangement, body portion 722 includes at least two bend points 728a and 728b that are separated by a section of shaft 730. Bend point 728a is positioned proximal of a distal end of body portion 722, defining a retaining section 732. Bend point 728b is positioned proximal of shaft section 730. Bend point 728b and a proximal end 734 cooperate to define a proximal shaft section 736. Bend points 728a and 728b serve to axially space retaining section 732 from proximal section 734. In one arrangement, as shown in FIG. 19D, shaft section 730 is disposed at an approximately 45° angle. In another exemplary arrangement (not shown), shaft section 730 may be oriented at an approximately 90° angle. It is also contemplated that shaft section 730 may be deposed at other angles. In some exemplary arrangements, bend points 728a, 728b may be eliminated such that retaining section 732 and proximal section 736 are arranged along a common axis. Retaining section 732, shaft section 730 and proximal section 736 may be integrally formed together, or constructed as separate elements that are connected together.

Retaining section 732 terminates at its distal end 738 in retaining member 726. As best seen in FIG. 19C, retaining member 726 is configured as a shepherd's hook that is configured to curve back toward retaining section 732, but defining a gap 740 between an end 742 of retaining member 726 and retaining section 732. Retaining member 726 may be integrally formed with retaining section 732, or formed as a separate component that connects with retaining section 732. Retaining member 726 is configured similar to a spring clip such that retaining member 726 snaps partially around outer sheath 102.

Mounted on proximal section 736 is engagement barrel 724. Engagement barrel 724 is configured for selectively rotation about proximal section 736. In one exemplary arrangement, on either end of engagement barrel 724, stop members 744 are disposed. In operation, engagement barrel 724 is positioned within Greenberg adapter and clamped thereto. Stop members 744 serve to prevent engagement barrel 724 from being unintentionally extracted from the Greenberg adapter. However, due to the configuration of engagement barrel 724 and placement of stop members 744, engagement barrel 724 is permitted to move a predetermined amount in a linear fashion. Moreover, because engagement barrel 724 is configured to selectively rotate about proximal section 736, outer sheath 102 may be selectively pivoted along the Y direction to a desired position. Further, because retaining member 726 is configured as a shepherd's hook with the gap 740, outer sheath 102 may be pivoted in the X direction. Thus holding arrangement 720 allows for selective positioning of outer sheath 102.

An alternative holding arrangement 750 is shown in FIGS. 19E-19F. Holding arrangement 750 is configured to be used with a Sugita adapter (not shown). Holding arrangement 750 is similar to holding arrangement 720 comprises body portion 752, an engagement barrel 754, and a retaining member 756.

Body portion 752 may be configured as a relatively thin shaft and may include one or more bend points 758a-758b. Like holding arrangement 720, bend points 758a, 758b serve to axially offset a retaining section 762 from a proximal section 764. A shaft section 760 is positioned between bend points 758a, 758b.

Retaining section 762 terminates at its distal end 768 in retaining member 756. As best seen in FIG. 19E, retaining member 756 is configured as a shepherd's hook that is configured to curve back toward retaining section 762, but defining a gap 770 between an end 772 of retaining member 756 and retaining section 762. Retaining member 756 may be integrally formed with retaining section 762, or formed as a separate component that connects with retaining section 762. Retaining member 756 is configured similar to a spring clip such that retaining member 756 snaps partially around outer sheath 102.

Mounted on proximal section 764 is engagement barrel 754. Engagement barrel 754 is configured for selectively rotation about proximal section 764. A mounting member 774 is fixedly secured to engagement barrel 754. Mounting member 774 is configured to be received within a Sugita clamp mechanism. In one exemplary arrangement, on a distal end of engagement barrel 754, a stop member 776 is disposed. In operation, engagement barrel 754 is positioned within the Sugita adapter and clamped thereto. Stop member 776 serves to prevent engagement barrel 754 from being unintentionally extracted from the Sugita adapter. However, due to the configuration of engagement barrel 754 and placement of the stop member 776, engagement barrel 754 is permitted to move a predetermined amount in a linear fashion. Moreover, because engagement barrel 754 is configured to selectively rotate about proximal section 764, outer sheath 102 may be selectively pivoted along the Y direction to a desired position. Further, because retaining member 756 is configured as a shepherd's hook with the gap 770, outer sheath 102 may be pivoted in the X direction. Thus holding arrangement 750 allows for selective positioning of outer sheath 102.

Yet another alternative arrangement of a holding arrangement 780 is shown in FIGS. 19G-19J. Holding arrangement 780 is configured to maintain longitudinal alignment of an exoscope 782 and outer sheath 102. In this arrangement, light is provided to outer sheath 102 (and hence to the surgical site/area of interest) via exoscope (Karl Storz Endoscopy, Germany) 782. Thus, while exoscope 782 is spaced apart from outer sheath 102, an effective visual line of sight and maintenance of projection of light to the bottom of outer sheath 102 may be achieved.

Holding arrangement 780 is provided with an alignment tool 784. Alignment tool 784 is configured with an outwardly extending arc portion 786. More specifically, outwardly extending arc portion 786 arcs away from a longitudinal axis LA that passes through a longitudinal space between exoscope 782 and outer sheath 102, when exoscope 782 and outer sheath 102 are aligned. In this manner, arc portion 786 cooperates with exoscope 782 and outer sheath 102 to define a working space between exoscope 782 and outer sheath 102. This arrangement permits a user to be able to pass instruments in and out of outer sheath 102, as well as the area of interest.

In one exemplary arrangement, arc portion 786 is defined by a pair of wire-like members 786a, 786b (best seen in FIG. 19H). Members 786a, 786b are configured to be substantially rigid so as to maintain the position of outer sheath 102 with respect to exoscope 782.

In addition to arc portion 786, alignment tool 784 further includes a exoscope attachment harness 788 and an outer sheath attachment arrangement 790. Exoscope attachment harness 788, best seen in FIG. 19H, is comprised of a retaining mechanism 792 attached to a reinforcement section 794. Reinforcement section 794 extends upwardly in the same direction as longitudinal axis LA from members 786a, 786b. Retaining mechanism 792 is configured to at least partially extend around an outer periphery of exoscope 782 in a snap-fit or clamping arrangement. In one exemplary arrangement, retaining mechanism 792 is integrally formed with reinforcement section 794. Similarly reinforcement section 794 may also be integrally formed with arc portion 786. A bend point 795 joins arch portion 786 with reinforcement section 794.

As best seen in FIG. 19I, outer sheath attachment arrangement 790 includes connector members 796a, 796b that are configured to be received within openings formed in grip ring 120, sufficiently spaced apart such that alignment tool 784 may maintain a desired position. In one exemplary arrangement, connector members are pins that are joined to members 786a, 786b by bend points 797a, 797b. With this arrangement, outer sheath 102 may be selectively pivoted about longitudinal axis LA, thereby allowing some degree of flexibility in positioning outer sheath 102 at the area of interest.

Referring to FIG. 19J, an alternative arrangement for connecting arc portion 786 to outer sheath 102 is shown. In this arrangement, an end of one of the members 786a is configured as a Shepard's hook 798, similar to that shown in the arrangements of FIGS. 19C and 19E. As explained above, this arrangement allows the outer sheath 102 to be pivoted in the X direction, thereby permitting selective positioning of outer sheath 102.

Outer sheath 102 is configured such that multiple instruments may be inserted simultaneously therewithin, thereby increasing the speed and safety of surgical procedures. In one exemplary arrangement, an endoscope may be partially inserted and held to one side of outer sheath 102, to provide an image of area of interest 500 to a monitor, while a surgical instrument, such as surgical instrument 640 is also inserted within outer sheath 102. Illuminating ring 300 may also be used, with the endoscope and the surgical instrument being inserted through access opening 308 that aligns with opening 146 of grip ring 120. Because illuminating ring 300 provides the necessary light for outer sheath 102, a relatively small diameter endoscope may be use, thereby increasing the available space within outer sheath 102 for other surgical instruments. In another exemplary configuration, the surgeon may have both a surgical instrument and a cautery instrument simultaneously inserted into outer sheath 102, thereby permitting the surgeon to cauterized vessels that are encountered during the procedure.

In another exemplary arrangement, during the procedure, fluorescing dye may be introduced into the patient, either before surgery or during the surgery. One such dye is Gliolan (5-Aminolevulinic Acid), however other suitable dyes may also be used. The fluorescing dye may be introduced by any suitable methods, including, but not limited to, injecting the patient with the dye, providing the dye orally to the patient prior to surgery, or even injecting the dye in situ through outer sheath 102. In one exemplary arrangement, the dye is configured to bond to proteins of abnormal cells such that the cells are visually distinguishable from healthy cells. With this visual indication of healthy vs. abnormal tissue, the surgical instrument may be more efficiently used to identify, as well as resect abnormal tissue. In other embodiments, light delivered through outer sheath 102 has a predetermined wavelength that is configured to interact with the dye to illuminate or fluoresce certain tissues. For example, illumination cap 300 may be provided with LED lights of a preselected wavelength that operatively interacts with a preselected dye to illuminate abnormal tissue and assist with differentiating healthy tissue from diseased tissue.

In another exemplary configuration, a light probe or fiber optic bundle (not shown) may be inserted into outer sheath 102 to assist with differentiation between healthy tissue and abnormal tissue. In one arrangement, the probe/bundle is simply inserted into outer sheath 102. The probe/bundle is operatively connected to a console such that the reflected light is delivered to the console. A sensor in the console (i.e., the sensor is remotely located from the point of detection, receives the reflected light to trigger a signal to the user based on predetermined parameters. In other words, the natural florescence of the tissue is then reflected back to the console to inform the user whether or not the tissue is diseased or abnormal. For those operations where debulking or tissue sampling is being conducted, the surgical device can be inserted into outer sheath 102 simultaneously with the probe/bundle, thereby improving the accuracy and efficiency of the debulking procedure.

Figure 20:
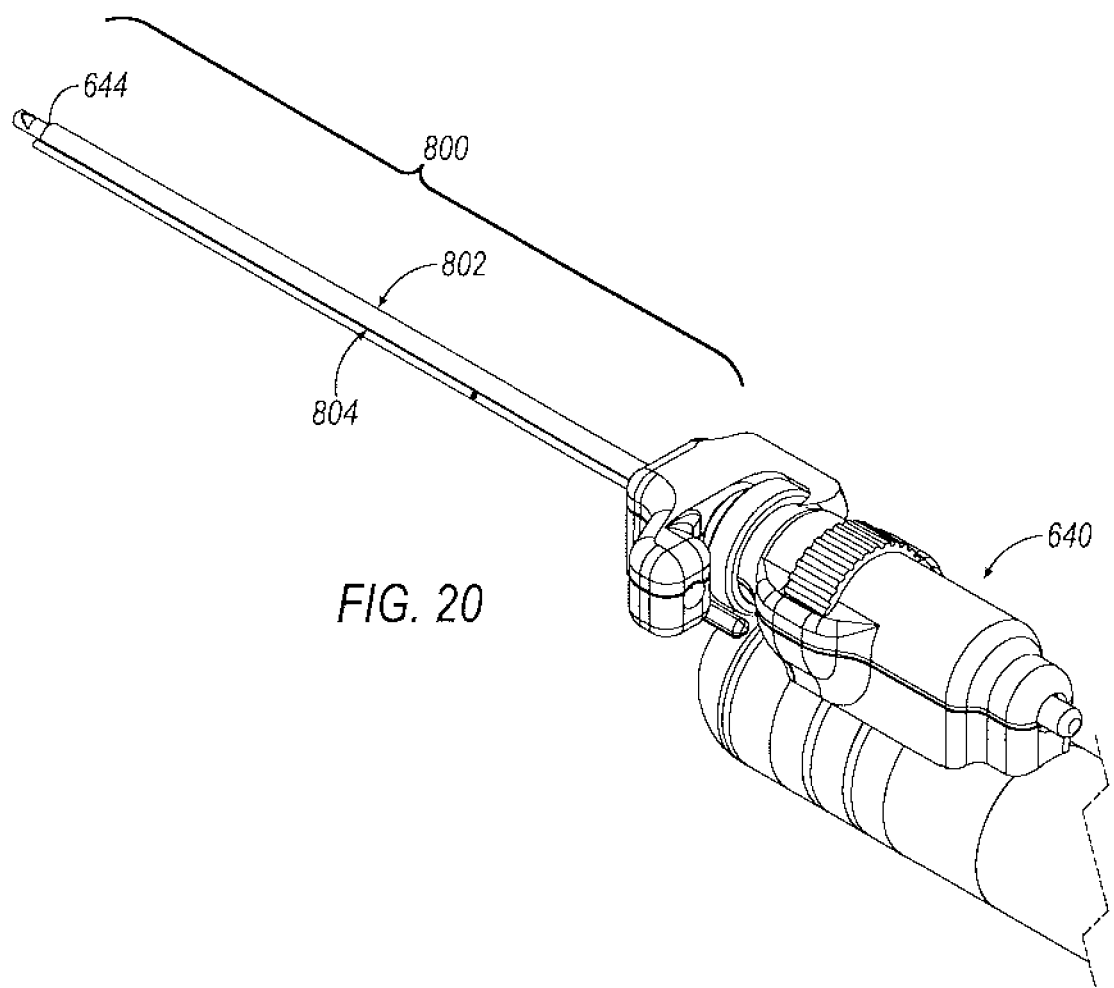
FIG. 20 is a partial perspective view of an exemplary delivery sleeve that may be used with a surgical device.

In another exemplary configuration, the surgical device may be further provided with a delivery sleeve 800 that mounts to surgical device 640, and example of which may be found in FIG. 20. Various embodiments of delivery sleeve 800 may be found in co-pending, and co-owned with the assignee of the present application, U.S. patent application Ser. No. 13/269,339, the contents of which are incorporated by reference in its entirety. As may be seen in FIG. 20, delivery sleeve 800 generally includes at least two lumens, a first lumen 802 which is configured to receive outer cannula 644 of surgical device 640, and a second lumen 804 which is configured to receive an optical device, such as a light probe or a fiber optic bundle (not shown). Use of this arrangement permits use of additional surgical tools/instruments within outer sheath 102. More specifically, as the optical device is supported within the delivery sleeve 800, which, in turn, is connected to the surgical device, the surgeon can simultaneously differentiate between abnormal and healthy tissue, and resect tissue, all with by just holding the surgical device 640. As a result, the surgeon may also choose to utilize a separate cautery device within outer sheath 102 to permit cauterization of any vessels during the resection, in real time, and without requiring removal of the surgical device 640.

Because outer sheath 102 may be directly positioned at area of interest 500 in such a manner as to avoid unnecessary damage to critical structures, and because surgical device 640 may be placed directly at the sight of area of interest, utilizing surgical access system 100 provides the ability to resect most of an area of interest 500, such a tumor. As one of ordinary skill in the art can appreciate, the more that a tumor is resected and removed, the less therapy is required for treatment. In other words, the more diseased tissue there is resected, the less diseased tissue there is to destroy.

In cases where cytoreduction is the objective to be performed, once resection of area of interest 500 has been completed, the process then proceeds to step 436. In step 436 a decision is made to either remove outer sheath 102 or to leave outer sheath 102 in position. More specifically, for some therapy applications, removal of outer sheath 102 may be more effective than leaving outer sheath in place to deliver the therapy. If the decision is made to remove outer sheath 102, after removal of outer sheath 102, the process 400 proceeds to step 438.

As one of ordinary skill in the art may appreciate, the natural elasticity of brain tissue will maintain access or a corridor to area of interest 500 for period of time, even after removal of outer sheath 102. In step 438, while the corridor is still intact after removal of outer sheath 102, in one exemplary arrangement, a delivery device may be inserted into the corridor to deliver irrigation to the surgical site. In some instances, a syringe may be inserted into the corridor to deliver an irrigating fluid, such as saline directly to the surgical site. In another exemplary configuration, a drainage catheter (which is configured with a plurality of small openings at its distal end) is delivered into the corridor such that the distal end of the catheter is placed at or adjacent the surgical site. Irrigating fluid is then introduced into the proximal end (such, as for example, by operatively attaching a syringe barrel to the proximal end), to deliver the irrigating fluid to the surgical site. The irrigating fluid flushes out debris and assists in the brain tissue's natural tendency to close back in on itself. Once the surgical site has been irrigated, it may also be desirable to deliver certain therapies directly to the surgical site, thereby avoiding therapy delivery and uptake issues traditionally encountered by systemic approaches. For example, certain therapies that may be provided in liquid form may be directly injected through the corridor, just prior to the tissue closing back in on itself. Because the corridor is closing, the therapy will be held in place at the surgical site, thereby increasing its effectiveness at the site and surrounding tissue.

In some therapy methodologies, outer sheath 102 may be necessary to aid in the delivery and/or placement of such therapy, as will be explained in further detail below. Accordingly, if the decision in step 436 is made to keep outer sheath 102 in place after completion of cytoreduction, the process 400 proceeds to step 442.

In step 442, area of interest/surgical site 500 is irrigated to again remove any debris from the area. Irrigation may be performed in the same manner as discussed in step 438, except through outer sheath 102. Once irrigation is complete, the process proceeds to step 444.

In step 444 a therapy is delivered to area of interest 500. In one exemplary configuration, intraoperative radiotherapy (IORT) may be employed, so as to deliver therapy directly to area of interest 500 through outer sheath 102. In one exemplary configuration, an implantable therapy may be applied to area of interest 500. Example of an implantable therapy include: bioabsorbable radiation pellets, wafers or mesh, such as, for example, those manufactured by Nano-Rad LLC. Other examples include, but are not limited to, titanium capsules or seeds with radiation contents, bioabsorbable gels or foams that contain radioactive, chemotherapy or immunotherapy agents.

In another exemplary configuration, a balloon catheter may be used to perform brachytherapy following the removal of diseased tissue at area of interest 500. For example, a balloon catheter may be inserted through outer sheath 102 and delivered to area of interest, and then the balloon catheter may be inserted with a predetermined amount of radioactive solution followed by the delivery of radiation to the surrounding tissues. A commercially available catheter that may be used includes the GliaSite balloon catheter, with an Iotrex radioactive solution. Use of a balloon catheter may provide a more targeted delivery of liquid radiation, thereby reducing impact on brain tissues surrounding the diseased tissue.

In another exemplary arrangement, an electron beam driven X-ray source may be provided. One such exemplary configuration is the Zeiss INTRABEAM®. The electrons are generated and accelerated in a main unit and travel via an electron beam drift tube which is surrounded by a conical applicator sheath such that its tip lies at an epicenter of an applicator sphere to provide a point source of low energy X-rays at the tip. With this configuration, a nearly isotropic field of low energy is emitted.

In operation, the applicator sheath is inserted through outer sheath 102 and into the surgical cavity at area of interest 500. An intraoperative ultrasound may be performed to determine the distance of the applicator surface to the skin, to avoid significant skin doses. The applicator sheath may be secured into place by the surgeon using subcutaneous sutures around the neck of the sphere, similar to that described above in connection with outer sheath 102.

In another exemplary arrangement, a photodynamic therapy may be used, whereby a predetermined chemical composition may provided to the patient and the chemical composition may be selectively activated by a predetermine wavelength, thereby achieving a therapeutic reaction. For example, in one exemplary configuration, illuminating ring 300 may be turned on to achieve the therapeutic reaction. In another exemplary configuration, a light source, such as, for example, a fiber optic bundle, may be directed through outer sheath 102, either directly through outer sheath 102 or through delivery sleeve 800.

In yet another exemplary configuration, external beam high frequency ultrasound or interstitial high frequency ultrasound may also be delivered through outer sheath and directly to area of interest 500.

Figure 21A:
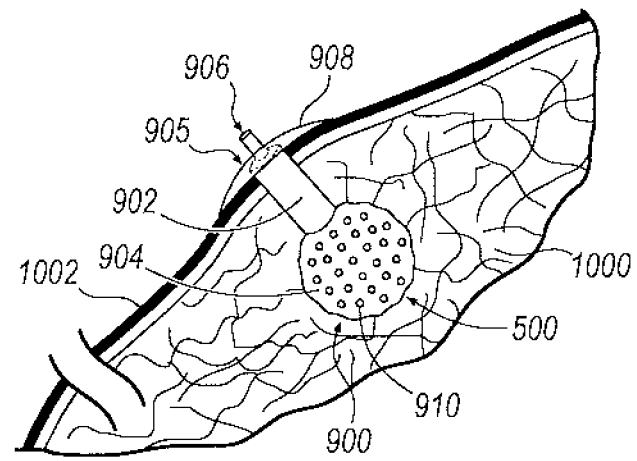
FIG. 21A is an exemplary arrangement for a therapy delivery device.
Figure 21B:
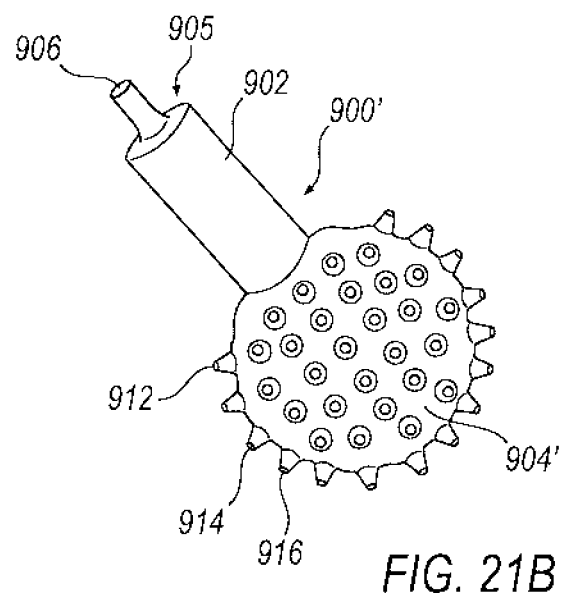
FIG. 21B is an alternative arrangement of the therapy delivery device of FIG. 21A.

In yet a further exemplary configuration, as shown in FIGS. 21A-21B, an implantable delivery device 900/900' may be provided. Implantable delivery device 900/900' includes a neck portion 902 that is connected to a body portion 904/904'. Both neck portion 902 and body portion 904/904' may be constructed of a relatively soft and flexible material. Body portion 904/904' defines a reservoir for holding a therapeutic agent therein. A proximal end 905 of neck portion 902 is largely closed, with access to an interior of implantable delivery device 900/900' being providing by a luer port 906. More specifically, therapy agents are introduced into delivery device 900/900' through luer port 906. A sealing flange 908 may further be provided, that operatively connects to neck portion 902 to assist in holding implantable delivery device 900/900' in place within the brain.

In the arrangement shown in FIG. 21A, body portion 904 may be provided with at least one small opening 910. In one exemplary arrangement, a plurality of small openings 910 are provided, and such openings may be spaced equi-distance from one another about the periphery of body portion 904. Small openings 910 are configured to permit the therapy agent that is introduced through luer port 906 to weep out of the reservoir formed by body portion 904 at a controlled rate to increase effectiveness. Alternatively, body portion 900 may be configured as a permeable membrane that permits slow and controlled passage of therapy from the reservoir to the brain tissue 1000.

In an alternative arrangement shown in FIG. 21B, body portion 904' may be provided with flexible finger-like projections 912. In one exemplary configuration, projections 912 are spaced equi-distance from one another about the periphery of body portion 904'. Projections 912 extend outwardly from an outer periphery of body portion 904' and may be formed with channels that provide communication between the reservoir and small openings 914 configured at distal tips 916 of projections 912. Openings 914 are configured to permit the therapy agent that is introduced through luer port 906 to weep out of the reservoir. Projections 914 assist in frictionally retaining delivery device 900' at a target site.

Referring back to process 400, if delivery device 900/900' is employed, delivery device 900/900' is inserted at area of interest 500 through outer sheath 102. Once positioned, outer sheath 102 is removed, and sealing flange 908 is operatively connected to neck portion 902 such that luer port 906 is accessible. Sealing flange 908 is configured to extend over the periphery of the surgical access opening that was formed through the skull 1002, thereby providing protection for the exposed brain tissue 1000. The therapeutic agent may be supplied to the reservoir formed by body portion 904/904' either before delivery device 900/900' is positioned at area of interest 500, or after sealing flange 908 is in place. Sealing flange 908, as well as body portion 904/904' and neck portion 902 may be configured with flexible material to allow for sealing against the dura and bone of the brain.

In yet another alternative arrangement involving delivery device 900/900', a transfer material may be delivered through outer sheath 102, similar to a foam that is configured to conform to the cytoreducted area of interest 500. The foam will allow continuous contact with the therapy agent that weeps through body portion 904/904' to provide a controlled dosage of therapy to area of interest 500.

After surgery and therapy on the target tissue is complete, the process proceeds to step 446. In this step, the instruments used for surgery and/or therapy are removed from outer sheath 102. As the target tissue is removed, brain tissue will naturally fill the void formed by removing area of interest 500 so that healthy brain tissue underlying the now removed target tissue is adjacent the end of outer sheath 102. Outer sheath 102 is then gently removed and the brain tissue will naturally fill and reclaim the space formerly occupied by the abnormality and outer cannula 102, aided by the irrigation of area of interest 500. Moreover, as the brain tissue reclaims the space formerly occupied by the abnormality and outer cannula 102, implanted therapies, such as, for example, bioabsorbable radiation pellets, wafers or mesh, will be held in place at area of interest 500 to provide effective treatment, all delivered and unencumbered by the limitations normally encountered attempting to cross the blood brain barrier. While this process may take several minutes, it is relatively atraumatic. Once outer sheath 102 has been removed, the process continues to step 448, whereby the dura, skull and scalp are then closed in a known manner and the process ends. In the exemplary cases whereby a treatment device may be implanted, full reclaiming of the space is delayed due to the implant until implant is explanted or absorbed.

Because the location of the area of interest will vary from patient to patient, in one exemplary arrangement, it is contemplated that surgical access system 100 will be provided as part of a kit. More specifically, it is contemplated that a set of multiple obturators 104 may be provided that have different lengths and/or diameters. The set may be provided in a container that is configured be sterilized, with obturators 104 secured therein. It is also contemplated that a set of manipulation tools 700/700' may also be provided with the kit, and that manipulation tools 700/700' may be positioned within the container for selective sterilization. Outer sheath 102 may be provided with the kit, in various lengths and diameters that correspond to the lengths and diameters of obturators 104 provided in the kit. However, in one exemplary arrangement, outer sheaths 104 are provided separately as single use devices, in sterilized pouches.

While the above-described system provides the advantage of creating direct access to an area of interest, including an area of interest in the subcortical space, thereby permitting debulking of the area of interest to reduce the biological load of the abnormal tissue, as well as delivery of therapy in-situ (without the encumbrance and limitations encountered with systemic therapy delivery), for certain diseases, additional subsequent therapy may be warranted for increased therapeutic benefits.

More specifically, to be able to define an effective subsequent treatment therapy cocktail that will be effective on newly evolved strain of cells and tissue or disease that "morphs", the abnormal tissue at the area of interest requires imaging to define the area of interest, needs to be accessed, requires interrogation (sampling with or without a cytoreductive debulking of the area) to determine an appropriate therapeutic cocktail for the newly evolved cells and tissue. This process may be required to be repeated at a specific time or at a variety of time intervals for the live of the patient to assure the appropriate management or cure of the disease.

In the case of functional diseases of the brain such as a Alzheimer's, Parkinson's, epilepsy, bi-polar, depression, etc., the cells and affected tissues may not change or morph after the initial treatment but it may be useful to subsequently, image, access, interrogate the tissue (sample or debulk) the same or another area of interest after the initial delivery of a therapy to determine the effectiveness of the previous application to determine the response of the tissues to the treatment regimen to determine the need for subsequent treatment regimens and the nature of the therapeutic treatment required for the subsequent therapy.

Figure 22:
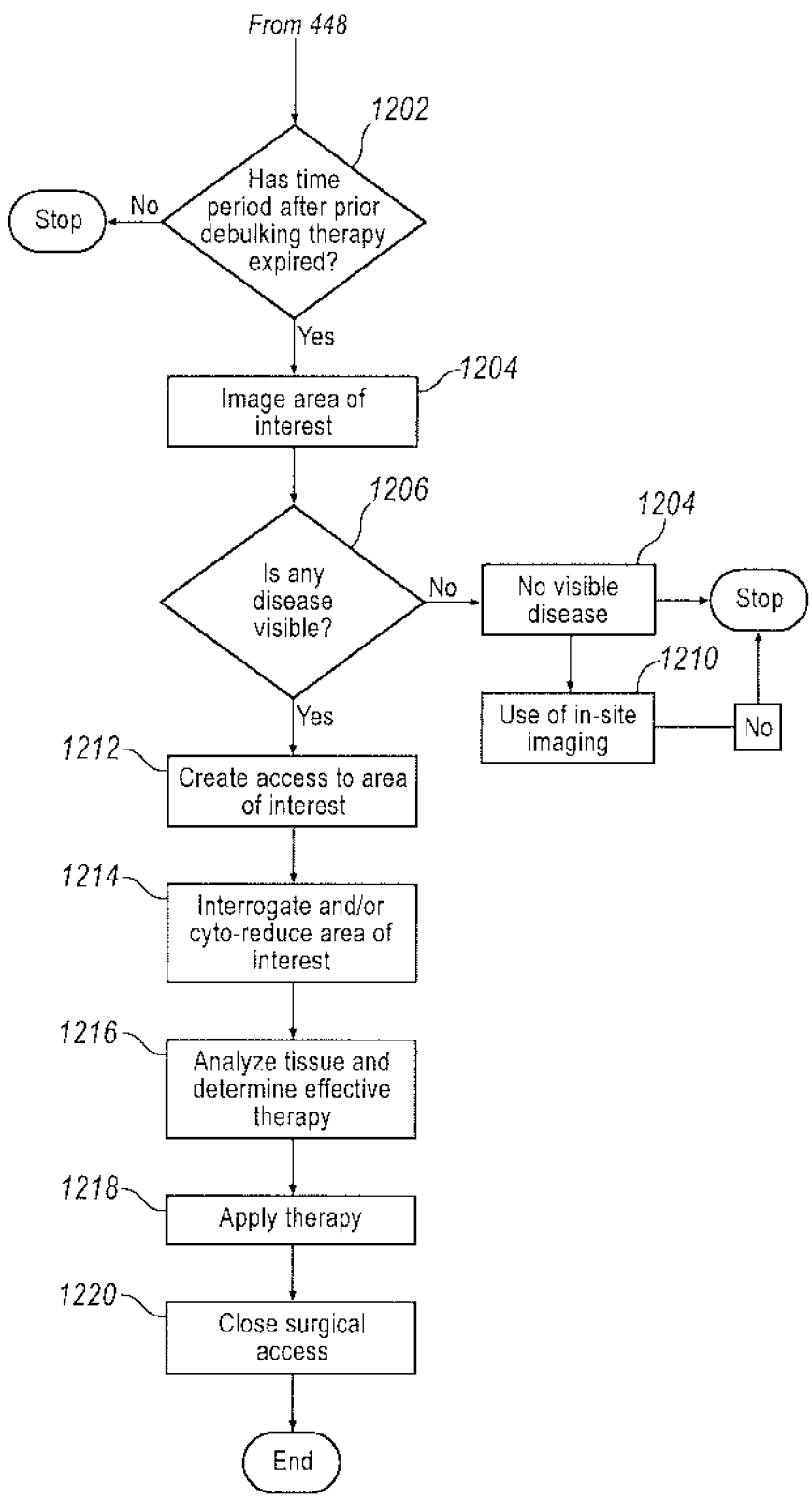
FIG. 22 is a flow chart illustrating a process flow for follow-up therapy whereby the surgical access assembly may be employed.

Referring to FIG. 22, a process flow 1200 illustrating an additional method of treatment is disclosed to address a second stage treatment regime. Process flow 1200 begins a predetermined time period 1202 after an initial resection and treatment process flow 400 (as shown in FIG. 13) has been completed. The need, if any, for process flow 1200 and the predetermined time period 1202 will depend on the effectiveness of the initial treatment and the nature of the disease being treated disease state-morphing, as well as the form of therapy that is originally applied. The process then proceeds to step 1204.

In step 1204, the area of interest 500 is re-imaged to determine the effects of therapy on area of interest 500. In other words, step 402 of process 400 is repeated. Such imaging includes, but is not limited to, MRI or CT imaging. The process then proceeds to step 1206.

In step 1206, a determination is made as to whether any disease is visible after employing the imaging step 1204. For certain diseases, if no visible disease is detected 1208, the process 1200 stops. For certain low-grade gliomas, for example, no more intervention may be required. For other diseases, i.e., fast growing tumors such as gliomas, if external imaging modalities fails to detect any visible disease, based on the patient history including prior disease pathology, it may be warranted to employ an in-situ imaging technique in step 1210. Some examples of such techniques include, but are not limited to spectroscopy, MRI, ultrasound, florescence. If, after completion of step 1210, no visible sign of disease are evident, the process stops. However, if after steps 1206 and 1210, the imaging step reveals visual evidence of disease, the process proceeds to step 1212.

Figure 13:
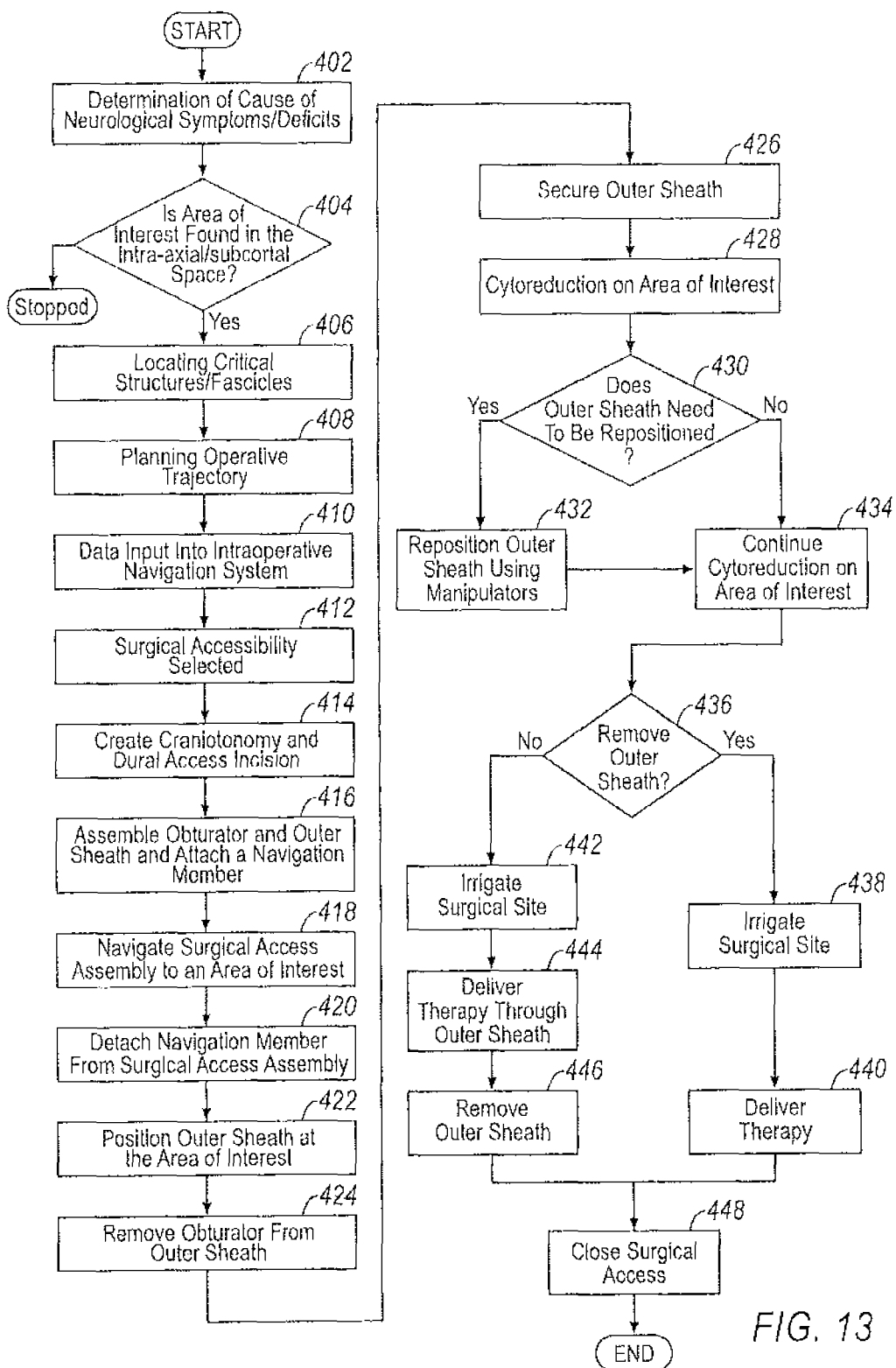
FIG. 13 is a flow chart illustrating a process flow using the surgical access assembly.

In step 1212, many of the steps of the process flow 400 set forth in FIG. 13 is repeated. More specifically, steps 406-426 of process flow 400 are repeated to create access to area of interest 500. Next the process proceeds to step 1214.

In step 1214, area of interest 500 is interrogated (such as, for example, via additional cyto-reduction or just sampled/biopsy), similar to steps 428-434 in FIG. 13. Indeed, after the initial treatment process, the disease may have mutated such that the disease may be of a slightly different variant of the diseased tissue that was originally treated. As such, use of the same therapeutic cocktail in in-situ may no longer be effective. Accordingly, step 1214 involves interrogating the area of interest 500 to gather and determine the necessary information regarding the tissue makeup of the area of interest 500. Next, the process proceeds to step 1216.

In step 1216, tissue from area of interest 500 is analyzed to determine the appropriate and effective therapy to treat area of interest 500. In other words, evaluation of differentiating cells from area of interest 500 may be utilized to provide the most effective treatment for the disease. In some instances, immunotherapy may be utilized, whereby tissue samples taken from area of interest 500 are used to determine and subsequently formulate a therapy of personalized medicine to the specific disease mutation identified and analyzed in step 1216. One exemplary, non-limiting type of such immunotherapy is taught and disclosed in co-pending U.S. application Ser. No. 13/352,069, the contents of which are hereby incorporated by reference in its entirety. Once an appropriate therapy is determined, the process proceeds to step 1218, whereby the therapy is applied to area of interest.

The therapy may be applied in any suitable manner. For example, in some instances, it may be necessary to remove the outer sheath to deliver the therapy, such as that taught in steps 438-440 in FIG. 13. In other situations, the outer sheath may remain in place and the chosen therapy may be delivered in a manner similar to steps 442-446 in FIG. 13.

Once therapy has been appropriately delivered, the process then proceeds to step 1220 whereby the surgical access is closed in a manner similar to that which has been previously described above in connection with step 448 in FIG. 13. However, it is understood that the process flow 1200 may be repeated as needed until the patient is deemed disease free or the disease is managed to a point whereby it is not life threatening.

As described above, while the process using surgical access assembly 100 has been described in connection with performing a surgical resection procedure and subsequent treatment methods, surgical access assembly 100 may also be utilized for locating, evaluating and treating a variety of CNS based disorders, such as functional diseases/abnormalities, metabolic/regulatory systemic conditions, addictions and pain management, without necessarily requiring surgical resection/debulking. More specifically, in such instances, surgical access assembly 100 is inserted into the brain at an area of interest, as discussed above, thereby providing a pathway to the area of interest. Once surgical access assembly 100 is delivered to the area of interest and obturator 104 is removed from outer sheath 102, the area of interest may be interrogated to assist in determining an appropriate treatment and/or therapy, or even the effectiveness of treatment or therapy previously utilized on the patient.

The interrogation of the area of interest may be conducted in any suitable manner. Examples of interrogation include, but are not limited to, tissue sampling and/or cytoreduction. In other embodiments, interrogation may include image based tissue interpretation technologies, such as, but not limited to MRI, CT, PET, ultrasound, fluorescence, spectroscopy, as well as all derivative sequences from a primary imaging modality.

In other words, interrogation of the area of interest permits evaluation of biological/cellular activity from area of interest 500 to evaluate a previously applied therapy, as well as provide the most effective treatment for the disease and/or abnormality. The evaluation resulting from the interrogation step permits a personalized treatment plan/therapy to be delivered to effectively manage or treat a patient's disease or disorder. After the interrogation step, as discussed above, to the extent additional therapy is needed, such therapy can be delivered through outer sheath 102 as discussed above or as is appropriate based upon the disease/abnormality.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical access system, comprising:
an outer sheath defined by an open distal end and an open proximal end with a hollow body portion extending therebetween that defines a working channel; an imaging system; and
a holding arrangement positioned between the outer sheath and the imaging system and aligning the imaging system with the working channel of the outer sheath and maintaining a fixed distance between the imaging system and the outer sheath,
wherein the holding arrangement is defined by first and second ends, and wherein the first end has an attachment harness connected thereto, and wherein the second end has an outer sheath attachment disposed on a second end thereof,
wherein the holding arrangement is defined by a pair of alignment members arranged in an arc-shaped configuration between the first and second ends.

2. The surgical access system of claim 1, wherein the attachment harness is configured to connect to the imaging system.

3. The surgical access system of claim 2, wherein the attachment harness has a semi-circular shape.

4. The surgical access system of claim 1, wherein the imaging system is an exoscope.

5. The surgical access system of claim 1, further comprising an obturator defined by a proximal end and a distal end, wherein the obturator is defined by a tapered distal tip, wherein the obturator is selectively positionable within the outer sheath such that the distal tip protrudes from the distal end of the outer sheath when in an introducing configuration.

6. The surgical access system of claim 5, further comprising a navigational element that is seated within the obturator.

7. The surgical access system of claim 6, wherein the navigational element is centered within the obturator.

8. The surgical access system of claim 6, wherein a distal end of the navigational element is axially offset from the distal tip of the obturator.

9. The surgical access system of claim 6, further comprising a locking member that is operatively connected to a proximal end of the obturator, the locking member selectively engaging the navigation element to lock the navigation element against movement and to lock the navigational element to the obturator.

10. The surgical access system of claim 5, wherein the distal tip is sized to close off the distal opening of the outer sheath when in the introducing configuration.

11. The surgical access system of claim 6, wherein the obturator further comprises a handle portion having a central access opening formed on a proximal end of the handle portion, the central access opening being in communication with a central channel therein, the central channel sized to receive the navigation element.

12. The surgical access system of claim 11, wherein navigation element extends proximally from the obturator when in an operational position and is operatively connected to a navigation system.

13. The surgical access system of claim 1, wherein the imaging system includes a light source, and wherein the light source is directed to the working channel of the outer sheath.

14. The surgical access system of claim 1, wherein the alignment members are spaced from each other and are arranged to be parallel to one another.

15. The surgical access system of claim 1, further comprising a reinforcement section positioned between the attachment harness and the alignment members, wherein the reinforcement section extends along an outside surface of the image system.

16. The surgical access system of claim 1, wherein the image system is axially fixed with respect to the distal end of the outer sheath.

* * * * *